United States Patent
Biadillah et al.

(10) Patent No.: US 9,101,375 B2
(45) Date of Patent: *Aug. 11, 2015

(54) FENESTRATION THROUGH FOREIGN MATERIAL

(71) Applicant: Baylis Medical Company Inc., Mississauga (CA)

(72) Inventors: Youssef Biadillah, Lausanne (CH); Amanda Hartley, Caledon (CA); Gareth Davies, Toronto (CA); Naheed Visram, Epsom (GB); Taras Juzkiw, Mississauga (CA); John Paul Urbanski, Toronto (CA)

(73) Assignee: BAYLIS MEDICAL COMPANY INC., Montreal, Quebec (CA)

( * ) Notice: Subject to any disclaimer, the term of this patent is extended or adjusted under 35 U.S.C. 154(b) by 18 days.

This patent is subject to a terminal disclaimer.

(21) Appl. No.: 14/100,576

(22) Filed: Dec. 9, 2013

(65) Prior Publication Data

US 2014/0100561 A1 Apr. 10, 2014

Related U.S. Application Data

(63) Continuation-in-part of application No. 13/286,041, filed on Oct. 31, 2011, now Pat. No. 8,623,005, which is a continuation-in-part of application No. 11/905,448, filed on Oct. 1, 2007, now Pat. No. 8,048,071.

(60) Provisional application No. 60/827,466, filed on Sep. 29, 2006, provisional application No. 61/448,578, filed on Mar. 2, 2011.

(51) Int. Cl.
A61B 18/18 (2006.01)
A61B 18/14 (2006.01)
A61B 8/12 (2006.01)

(Continued)

(52) U.S. Cl.
CPC .............. *A61B 18/1492* (2013.01); *A61B 8/12* (2013.01); *A61B 19/24* (2013.01); *A61B 2018/00083* (2013.01); *A61B 2018/00214* (2013.01); *A61B 2018/00351* (2013.01); *A61B 2018/00702* (2013.01); *A61B 2018/00827* (2013.01); *A61B 2018/00875* (2013.01); *A61B 2018/00898* (2013.01); *A61B 2019/2292* (2013.01); *A61B 2019/465* (2013.01); *A61B 2019/5255* (2013.01);

(Continued)

(58) Field of Classification Search
CPC ...... A61B 18/18; A61B 18/1492; A61B 8/12; A61B 2018/00083; A61B 2018/00214; A61B 2018/00702; A61B 2018/00827; A61B 2018/00875; A61B 2018/00898; A61B 2018/00351
USPC ...................................... 606/20–52, 167, 170
See application file for complete search history.

(56) References Cited

U.S. PATENT DOCUMENTS

| | | | | |
|---|---|---|---|---|
| 6,562,031 B2 * | 5/2003 | Chandrasekaran et al. | .... | 606/41 |
| 7,828,796 B2 * | 11/2010 | Wong et al. | ...................... | 606/45 |
| 2007/0066975 A1 * | 3/2007 | Wong et al. | ...................... | 606/45 |

*Primary Examiner* — Joseph Stoklosa
*Assistant Examiner* — Amanda Scott
(74) *Attorney, Agent, or Firm* — Nir Lifshitz; Glenn Arnold

(57) ABSTRACT

Described herein is a method for creating a channel through a foreign material located in a septum of a heart at the site of a septal defect. The foreign material defines a material first surface and a substantially opposed material second surface, and the channel extends through the foreign material at least partially between the material first and second surfaces. The method uses an apparatus including an electrode and includes the steps of: positioning the electrode substantially adjacent to the material first surface; energizing the electrode with a radiofrequency current; and using the electrode energized with the radiofrequency current to deliver energy into the foreign material to create the channel.

31 Claims, 22 Drawing Sheets

(51) Int. Cl.
*A61B 18/00* (2006.01)
*A61B 19/00* (2006.01)
*A61F 2/06* (2013.01)

(52) U.S. Cl.
CPC .......... *A61B 18/18* (2013.01);*A61B 2019/5285* (2013.01); *A61B 2019/5466* (2013.01); *A61F 2002/061* (2013.01)

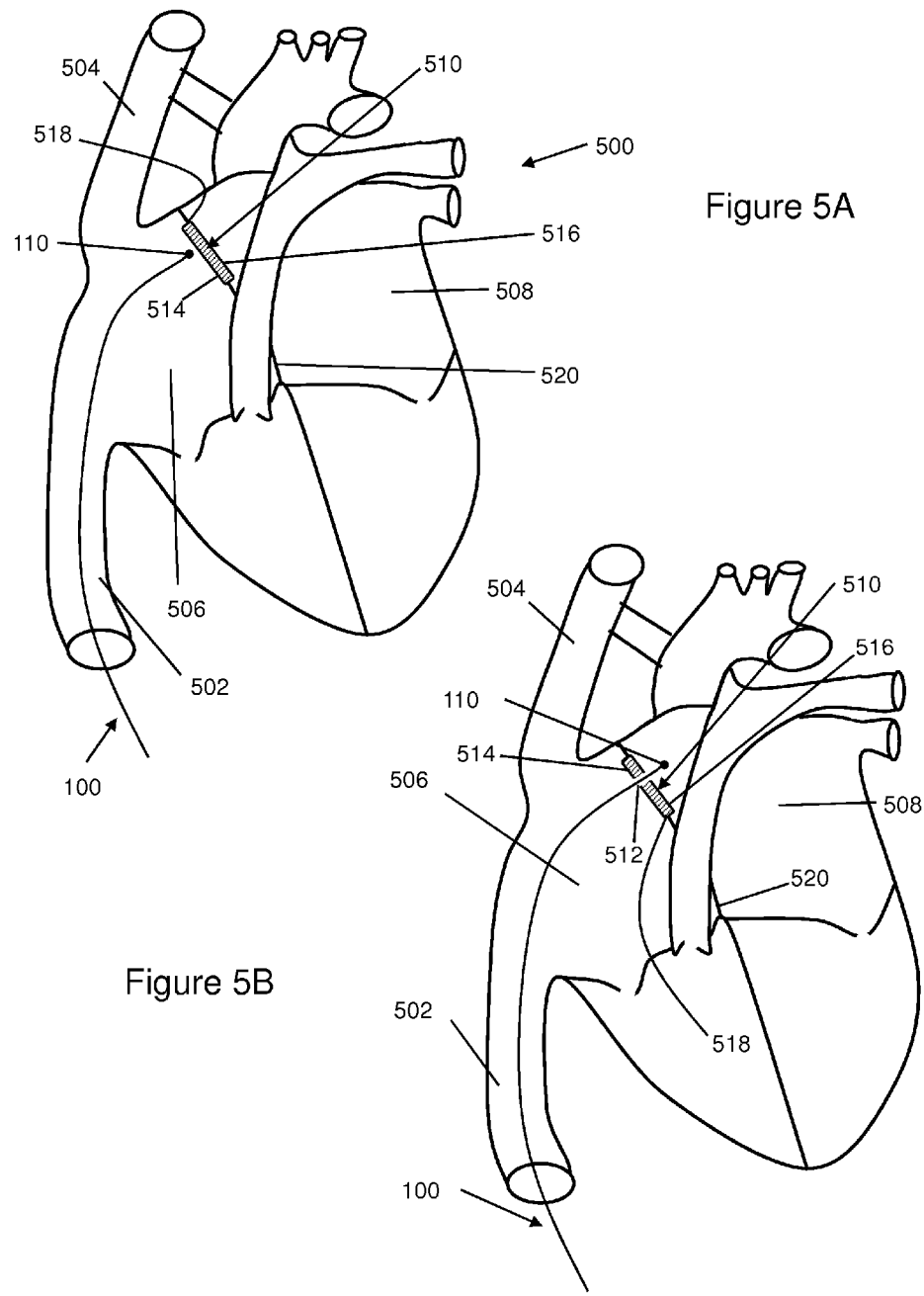

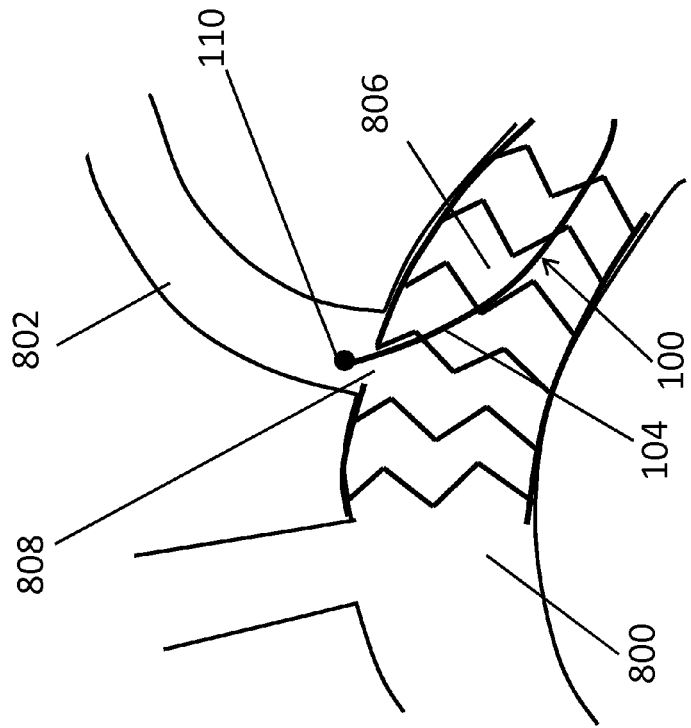
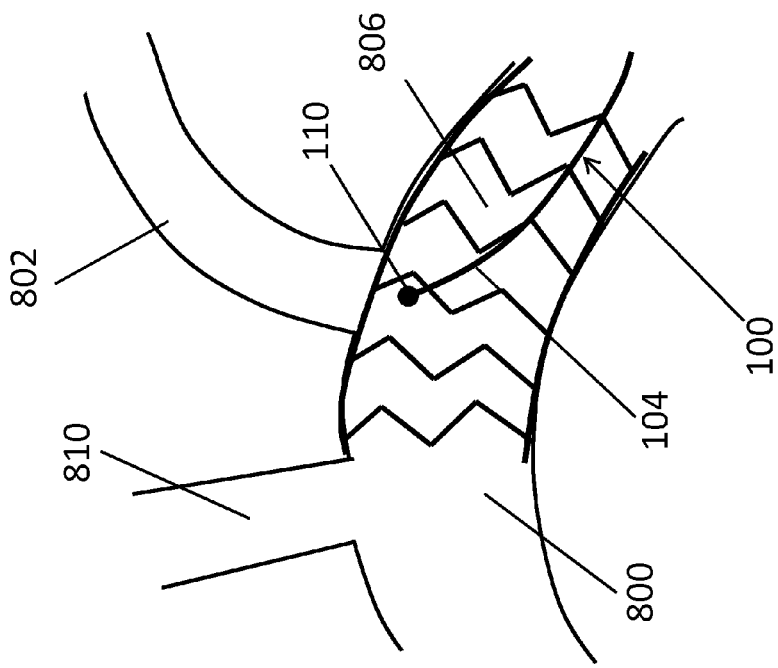
Figure 9B
Figure 9A

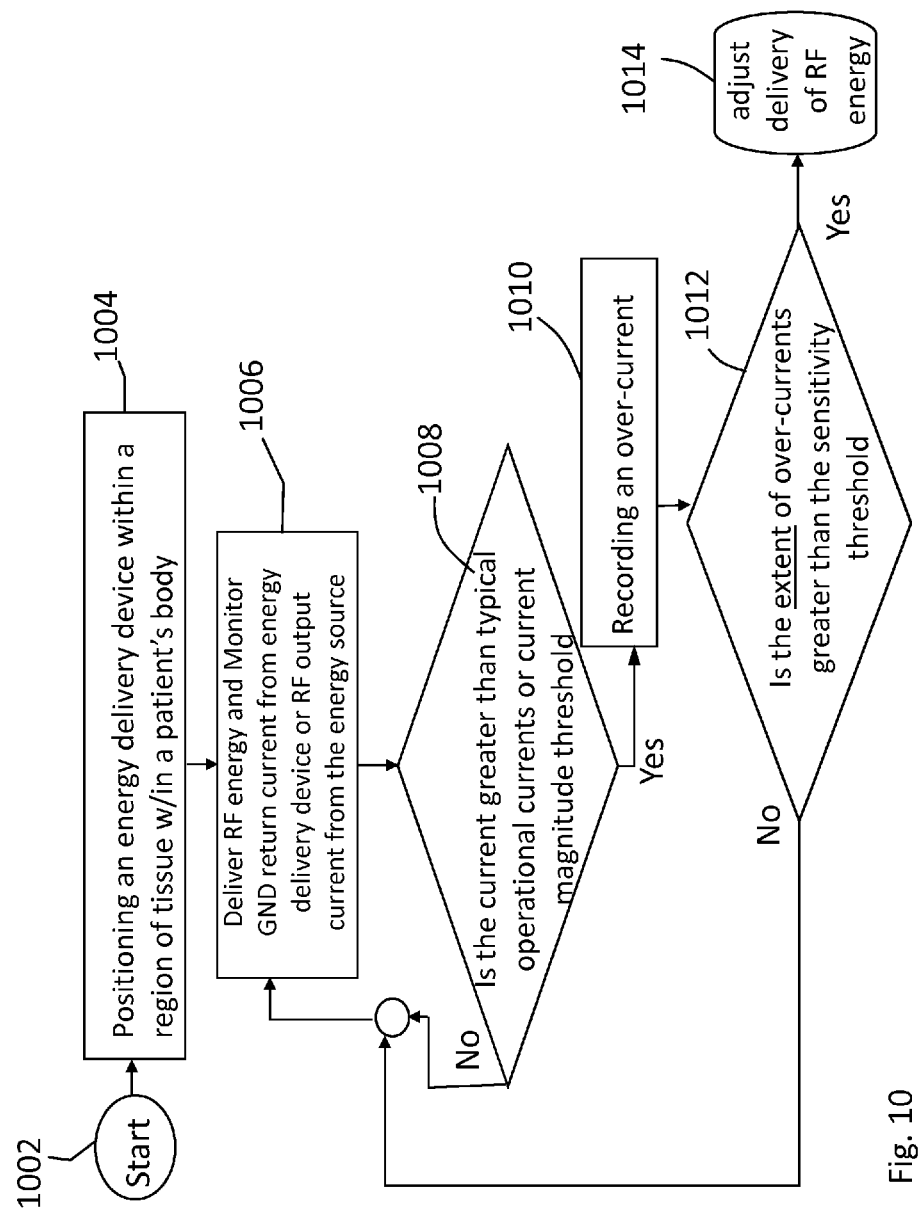

FENESTRATION THROUGH FOREIGN MATERIAL

CROSS-REFERENCES TO RELATED APPLICATIONS

This application is a continuation in part of U.S. patent application Ser. No. 13/286,041, filed on 31 Oct. 2011, which is a continuation-in-part of U.S. patent application Ser. No. 11/905,448, now U.S. Pat. No. 8,048,071, filed on Oct. 1, 2007, which claims the benefit of U.S. provisional patent application Ser. No. 60/827,466 filed on 29 Sep. 2006. U.S. patent application Ser. No. 13/286,041, further claims the benefit of U.S. provisional application No. 61/448,578, filed on Mar. 2, 2011. All of these US patent applications and provisional patent applications are hereby incorporated by reference in their entirety.

FIELD OF THE INVENTION

The present invention relates generally to methods and devices usable to deliver energy within the body of a patient. More specifically, the present invention is concerned with a method for creating a channel through foreign material.

SUMMARY OF THE INVENTION

There are certain situations in which it would be desirable to create a channel through foreign material located in a body of a patient. More specifically, foreign material may be positioned within a septum of the heart to treat a septal defect. A septal defect is a form of congenital heart defect that enables blood flow between two compartments of the heart, for example between the left and right sides of the heart. A specific example of a septal defect is an atrial septal defect along the inter-atrial septum (also referred to as the atrial septum) between the left and right atria of the heart. Normally, the right and left atria are separated by the atrial septum. If there is a hole or aperture through the atrial septum, then oxygenated blood can flow directly from the left side of the heart to mix with the deoxygenated blood in the right side of the heart, or vice versa. This may lead to lower oxygen levels in the arterial blood that supplies the brain, organs, and tissues and may additionally lead to other complications such as risk of embolisms, or even heart failure or death. Foreign material may be placed within the septum, such as within an occluder, to treat the septal defect by preventing the passage of blood between the left side of the heart and the right side of the heart. An occluder may be positioned within the septum using percutaneous means which may reduce procedural complexity and reduce recovery times for patients. As such it may be the first choice of treatment for treating a septal defect.

In some circumstances, patients that have previously undergone a procedure for placing foreign material, such as within an occluder within the heart to treat a septal defect, may require access to the left side of the heart for additional procedures to treat anomalies on the left side of the heart. For example, access to the left atrium or ventricle may be required for corrective cardiac ablation procedures or other procedures such as mitral valve repair. However, once the septal defect is sealed by the foreign material, it may be difficult to access the left side of the heart using conventional techniques that are often used to puncture through the septum mechanically. This is partially due to the fact that the natural path of the mechanical apparatus through the septum may now be obstructed by the foreign material. More specifically, the foreign material included in an occluder may be difficult to cross using conventional mechanical puncturing techniques, for example with a percutaneous mechanical needle, because of the relatively large forces required. Also, the relatively large forces exerted onto the needle may pose an additional risk that the needle will pass through the foreign material suddenly in an uncontrolled manner and damage adjacent tissues within the left side of the heart.

The present inventors have described a method for providing access to the left side of the heart in patients that have previously had a septal defect repaired with foreign material which may be included, for example, within an occluder. In contrast to the commonly understood mechanisms of energy-based perforation it has been unexpectedly found that, as described further herein below, a radiofrequency-based apparatus is usable to create channels through foreign materials including foreign material included within the septum of a patient. In some cases, the foreign material may be, substantially synthetic materials. Thus, the proposed method of the present invention involves using an apparatus having an electrode for delivering radiofrequency energy to create a channel through foreign material for example within an occluder positioned within the septum of the heart.

The methods of the present invention provide a surprising and unexpected result in that energy, for example radiofrequency electrical energy, is usable to create a channel in foreign material within the body of the patient, including, for example, synthetic material substantially not composed of cellular-based biological tissue (although it may, in some embodiments, be covered with live cells if, for example, it has been implanted in the body for a sufficient amount of time). In addition, embodiments of the present invention may minimize the risk of accidental puncture or perforation of a blood vessel or other bodily structure. Furthermore, embodiments of the present invention provide for the creation of a channel without requiring a mechanical tear of the foreign material. The methods of the present invention may also be useful in other applications, including, in general, wherever foreign material in a patient's body should be penetrated.

More specifically, in accordance with a first broad aspect, the present invention provides a method for creating a channel through a foreign material located in a septum of a heart at the site of a septal defect, said foreign material defining a material first surface and a substantially opposed material second surface, said channel extending through said foreign material at least partially between said material first and second surfaces, said method using an apparatus including an electrode, said method comprising: positioning said electrode substantially adjacent to said material first surface; energizing said electrode with a radiofrequency current; and using said electrode energized with said radiofrequency current to deliver energy into said foreign material to create said channel.

As a feature of this broad aspect, the foreign material is included within an occluder extending across the septum at said septal defect. As an example of this feature the septum is selected from the group consisting of an atrial septum and a ventricular septum. As an additional example of this feature, the occluder comprises one or more discs that are coupled by a bridging component.

In some embodiments the channel comprises one or more channel portions. In some examples of this the apparatus is used to create at least one of the one or more channel portions within one of said one or more discs.

In a further example of this, the apparatus is used to create at least one of the one or more channel portions within each of said one or more discs. In some embodiments said one or more channel portions are substantially aligned. In one instance of this, at least one of said one or more channel portions extends through said bridging component.

In other embodiments, the foreign material forms one or more graft portions of each of the one or more discs, and wherein each of the one or more discs comprises: a supporting structure that is associated with the one or more graft portions for supporting the one or more graft portions.

In one particular example, the supporting structure comprises a metal scaffold.

As another example said one or more graft portions comprise one or more layers. In one instance of this example said one or more layers are spaced apart from one another. In another instance of this example said one or more layers comprise a synthetic material.

In some such embodiments, said synthetic material is selected from the group consisting of a polyester, an expanded polytetrafluoroethylene (ePTFE), and a polyethylene terephthalate (PET) and fabrics thereof. In one example, said synthetic material comprises a woven polyester. In some instances said woven polyester is selected from the group consisting of a monofilament twill woven fabric and a multifilament tubular woven fabric. In another example, said one or more layers comprise expanded polytetrafluoroethylene (ePTFE).

As another feature of the broad aspect, the step of delivering energy comprises generating a vapor layer around the electrode to facilitate arcing to create said channel within said foreign material. As an example of this feature, the step of delivering energy comprises delivery of thermal energy to substantially melt said foreign material to create said channel therein. In a specific instance of this example, said foreign material comprises a synthetic material embedded within tissue. In some such embodiments, the step of delivering thermal energy comprises transfer of thermal energy into said foreign material via the tissue upon energizing said electrode with said radiofrequency current.

As another feature of this broad aspect, the step of positioning said electrode substantially adjacent to said material first surface comprises positioning said electrode substantially in contact with said material first surface to allow said electrode to substantially melt said foreign material upon energizing said electrode with said radiofrequency current.

In some embodiments said method further comprises the steps of: detecting if said electrode is positioned adjacent said metal scaffold; and upon detecting that said electrode is positioned adjacent said metal scaffold, guiding the apparatus away from the metal scaffold to be positioned adjacent said foreign material.

In one example, the method of further comprises the steps of: stopping the delivery of energy prior to guiding the apparatus away from the metal scaffold; and re-energizing said electrode once it is positioned adjacent said foreign material.

In another example, the step of detecting if said electrode is positioned adjacent said metal scaffold uses a technique taken from the group consisting of: measuring output impedance, measuring output current, obtaining tactile feedback and using imaging techniques.

In still another example, the step of detecting if said electrode is positioned adjacent said metal scaffold is performed substantially automatically.

In a further example, said occluder comprises a single wire frame metal scaffold around a periphery thereof and wherein the step of guiding the apparatus away from the metal scaffold involves guiding the apparatus away from the periphery of the occluder.

In accordance with another broad aspect embodiments of the present invention provide a method of gaining access into a left side of a heart, the heart having a septum wherein said septum comprises a septal defect, the heart further including an occluder extending across said septum to repair said septal defect, said occluder comprising foreign material, said method using an apparatus including an electrode, said method comprising: positioning said electrode substantially adjacent to said foreign material within said occluder; and delivering energy into said foreign material using by energizing said electrode with radiofrequency current to create a channel within said foreign material to allow the apparatus to cross the septum through said channel to gain access into the left side of the heart.

As a feature of this broad aspect, the step of positioning said electrode comprises gaining access into the heart by inserting the apparatus through the inferior vena cava. As another feature of this broad aspect, the step of positioning said electrode comprises gaining access into the heart by inserting the apparatus through the superior vena cava.

Other objects, advantages and features of the present invention will become more apparent upon reading of the following non-restrictive description of preferred embodiments thereof, given by way of example with reference to the accompanying drawings.

BRIEF DESCRIPTION OF THE DRAWINGS

In the appended drawings:

FIGS. 5A and 5B, in schematic views, illustrate a method for creating a channel in a septal patch extending across an aperture formed in the heart of a patient in accordance with an embodiment of the present invention;

FIGS. 9A and 9B, in schematic view illustrates a method for creating a channel in a stent graft extending across an ostium of a left Subclavian Artery (LSA) of a patient in accordance with an alternative embodiment of the present invention; and FIG. 10 is a flow chart showing steps of a method in accordance with an embodiment of the present invention.

DETAILED DESCRIPTION

Figure 1A:
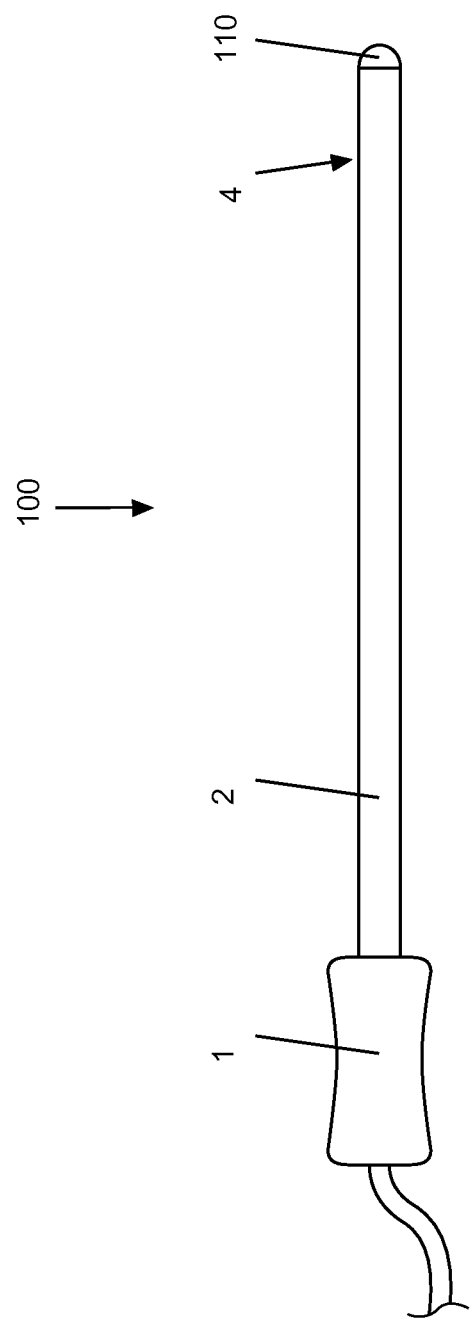
FIG. 1A, is side view of an apparatus for creating a channel through a foreign material in accordance with an embodiment of the present invention.

In accordance with an embodiment of the present invention, a method is provided for creating a channel through foreign material that has been included within a septum of the heart for repairing a septal defect such as through an occluder positioned within the septum of the heart. In these patients, access may be required from the right side of the heart into the left side of the heart through the septum to treat a condition affecting the left side of the heart. However, the presence of the foreign material within the septum creates a challenge for traversing the septum. The proposed method of the present invention involves using an apparatus having an electrode for delivering radiofrequency energy to create a channel through the foreign material. As such, the method of the present invention provides access to the left side of the heart in patients that have previously had a septal defect repaired with foreign material.

More specifically, in accordance with a first broad aspect, the present invention provides a method for creating a channel or fenestration through foreign material positioned within a region of tissue within a patient's body. Some embodiments of the present invention provide for a method of creating a channel through foreign material positioned within a septum within a patient's heart, as discussed further in detail with reference to FIGS. 5A-5I.

In other embodiments, a method is provided for creating a channel through a stent graft located in a body of a patient. The stent graft may include foreign material defining a material first surface and a substantially opposed material second surface and the channel extends through the foreign material between the material first and second surfaces. Typically, the method uses an apparatus including a substantially elongated member defining a proximal end region and a substantially longitudinally opposed distal end region, the substantially elongated member including an electrode located about the distal end region.

The method includes positioning the electrode substantially adjacent to the material first surface; energizing the electrode with a radiofrequency current; and using the electrode energized with the radiofrequency current to deliver energy into the foreign material to create the channel.

For example, the method is usable for restoring blood flow to a blood vessel of a body of a human or animal, the blood vessel being occluded by a foreign material. In this case, the channel is created through the foreign material.

As a feature of the aforementioned aspects, in some embodiments of the invention, the apparatus has a substantially atraumatic distal end, thus reducing the risk of unintentional perforation of a body vessel or other tissues. Also, the use of energy in creating the channel allows for the creation of channels in foreign materials through which creation of such channels is difficult, if not impossible, to perform using mechanical force. In some embodiments, the method is performed using relatively small apparatuses, for example apparatuses having a relatively small diameter, which are therefore relatively easily introduced into relatively small vessels.

With specific reference now to the drawings in detail, it is stressed that the particulars shown are by way of example and for purposes of illustrative discussion of embodiments of the present invention only, and that many alternative embodiments of the invention are within the scope of the appended claims.

For the purposes of this description, the term 'proximal' indicates next to or nearer to the user, and the term 'distal' indicates further away from the user, when the apparatus is in use.

Apparatus

Structure

In accordance with some embodiments of the present invention, an apparatus is provided for creating a channel through foreign material positioned in a patient's body. The apparatus is functional to deliver radiofrequency energy to create the channel within the foreign material. In one particular example, the apparatus 100 is an NRG® Transseptal Needle available from Baylis Medical Company Inc. The NRG® Transseptal Needle is usable with a BMC Radiofrequency Puncture Generator in order to deliver radiofrequency (RF) energy, such as RFP-100 or RFP-100A generators also available from Baylis Medical Company Inc. The NRG® Transseptal Needle sold by Baylis Medical Company Inc. is a relatively stiff needle that may be particularly suitable for use in transseptal procedures, for example to create a channel through foreign material within a septum of the heart. For example, as discussed in further detail herein below, with respect to FIGS. 5A-5I. The stiffness of the NRG® Transseptal Needle allows for ease of positioning it at the septum of the heart and allows for sufficient force transmission to create a channel through the foreign material at the septum. Some embodiments of the NRG® Transseptal Needle are shown in FIGS. 1A-2D. FIG. 1A is a side view of an apparatus 100 in accordance with an embodiment of the present invention. In general the apparatus 100 comprises a handle 1, a shaft or elongated member 2, and a distal end region or distal portion 4 of elongated member 2. A functional tip that has an electrode 110 that is operable to deliver energy is associated with the distal tip of distal portion 104.

The embodiment of FIG. 1A has an electrode 110 that is dome-shaped, while alternative embodiments may have an electrode 110 that has a different shape, for example (but not limited to), pointed or knife-like. The internal details of elongated member 2 of FIG. 1A may vary. An example of elongated member 2 of FIG. 1A may include a plastic shaft that contains a wire connected to distal electrode 110, while an alternative example of elongated member 2 of FIG. 1A may include an electrically conductive metal tube covered with electrical insulation. In other alternative embodiments, elongated member 2 may comprise a coil, braid or a conduit that is not round. The part of the device that is normally inserted into a patient (the usable part of the device) generally includes (but is not limited to) elongated member 2 and the functional tip. Embodiments of the disclosure include a lumen inside elongated member 2 for fluid flow such that fluid can be delivered or removed through the lumen (or conduit), or used for pressure sensing. The fluid may be gas, liquid, or particles of solid that can flow. Echogenic marker beads are an example of particles of solid that may flow.

Figure 1B:
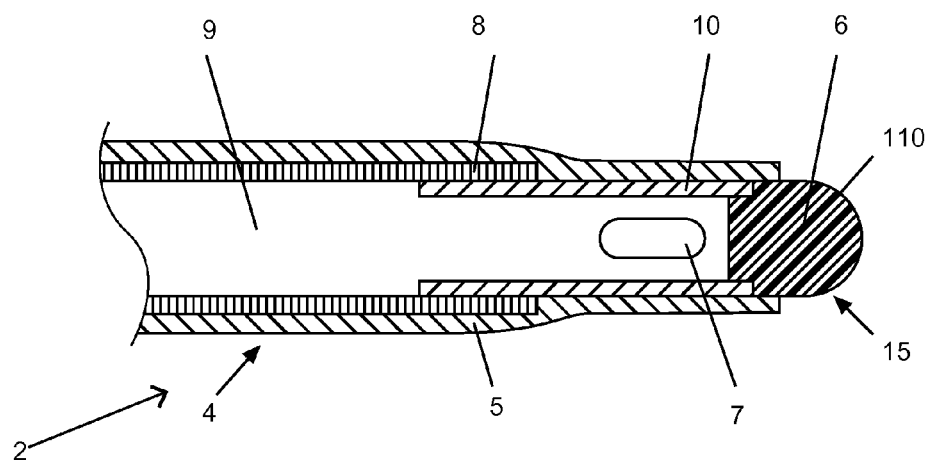
FIG. 1B, is a cut-away view of a distal portion of an apparatus in accordance with an embodiment of the present invention.

With reference now to FIG. 1B, an embodiment of the invention includes an elongated member 2 that is comprised of a metal tube 8 which is in electrical communication with metal end member 10. Insulating layer 5, which may be PTFE (polytetrafluoroethylene), covers metal tube 8 and some of end member 10, leaving a distal portion of metal end member 10 exposed to define an electrode 110. Metal tube 8 and metal end member 10 can be comprised of, but are not limited to, stainless steel. The distal end of end member 10 includes a functional tip 15 that includes the aforementioned electrode 110 and a radiopaque marker 6.

A possible method to produce functional tip 15 includes inserting radiopaque filler (or other radiopaque material) inside the distal end of end member 10 and then fusion welding said distal end to close off lumen 9 at the end of end member 10. The radiopaque filler may comprise platinum, iridium, gold palladium, tungsten, or other radiopaque metal or alloys thereof, such as for example an alloy of about 90% platinum and about 10% iridium or an alloy of about 92% platinum and about 8% tungsten. The portion of functional tip 15 extending beyond insulating layer 5 functions as electrode 110. The radiopaque part of the fusion welded material forms radiopaque marker 6. Depending on how far distally insulating layer 5 extends along distal portion 4, part, all, or none of radiopaque marker 6 can be covered by the insulating layer. Consequently, electrode 110 can possibly contain part, all, or none of radiopaque marker 6. The configuration of the metals in the fusion weld can vary depending on a number of factors related to the welding process, some (but not all) of the factors including: the amount and type of radiopaque filler used in making the weld, the thickness and type of metal of end member 10, the period of time that energy is applied to the materials, and the energy level.

Additional features of this embodiment include a lumen 9 and a lateral aperture (side port opening) 7 for movement of fluid between the lumen and the environment outside of the device. Lumen 9 is blocked (or closed) at the distal end of end member 10 by functional tip 15. Opening 7 is closer to the proximal end of elongated member 2 than is functional tip 15, whereby functional tip 15 does not obstruct fluid flowing through opening 7. Electricity may be delivered through metal tube 8 and end member 10 to electrode 110. The embodiment of FIG. 1B is an example of an embodiment of the invention having an imaging marker 6 that is more distal than the opening (exit port) through which fluid may exit or enter the lumen of the device. Several views of an additional embodiment are shown in FIGS. 2A-2D. These views illustrate electrode 110 and marker 6 of a functional tip 15, a metal tube 12, aperture 7, lumen 9, and insulating layer 5.

With reference to FIG. 1B, and FIGS. 2A-2D, the medical apparatus of the disclosure may be used with a source of radiofrequency (RF) energy for creating a channel at a target location in a body of a patient. One embodiment of such a method comprises the steps of: a) introducing an apparatus 100 having an elongated member 2 and a functional tip 15 into the vasculature of a patient, b) advancing elongated member 2 through the vasculature using radiopaque marker 6 of functional tip 15 for imaging whereby functional tip 15 (which has an electrode 110) can be guided or directed, c) positioning electrode 110 of functional tip 15 (which is operable to deliver energy) at the target location, and d) delivering electrical energy through electrode 110 to create the channel.

Features of the apparatus 100 provide certain advantages during use. For example, the opening (aperture) 7 can be used to deliver fluid from the lumen 9 of the elongated member 2 to the target location. In some embodiments, having the distal end of lumen 9 closed by functional tip 15 and having an opening 7 that is a side port helps to prevent coring of tissue when creating the channel. This embodiment includes functional tip 15 having a diameter that is less than the outer diameter of the elongated member 2 to ease or facilitate the advancement of the elongated member through vasculature i.e. the functional tip does not increase the outer diameter of the device which would make advancement more difficult. In alternative embodiments, functional tip 15 may have a portion of it visible under alternative medical imaging modalities, for example, ultrasound or magnetic resonance.

Additionally, visualizing the marker 6 of the functional tip 15 using medical imaging, may facilitate positioning apparatus 100 at the target site adjacent the foreign material. A variety of additional steps may be performed as part of the method, such as measuring one or more properties of the target site, for example an electrogram or ECG (electrocardiogram) tracing and/or a pressure measurement, or delivering material to the target site, for example delivering a contrast agent through aperture(s) 7 and/or an open distal end. Such steps may facilitate the localization of the electrode 110 at the desired target site. In addition, tactile feedback provided by apparatus 100 is usable to facilitate positioning of the electrode 110 at the desired target site.

Figure 2A:
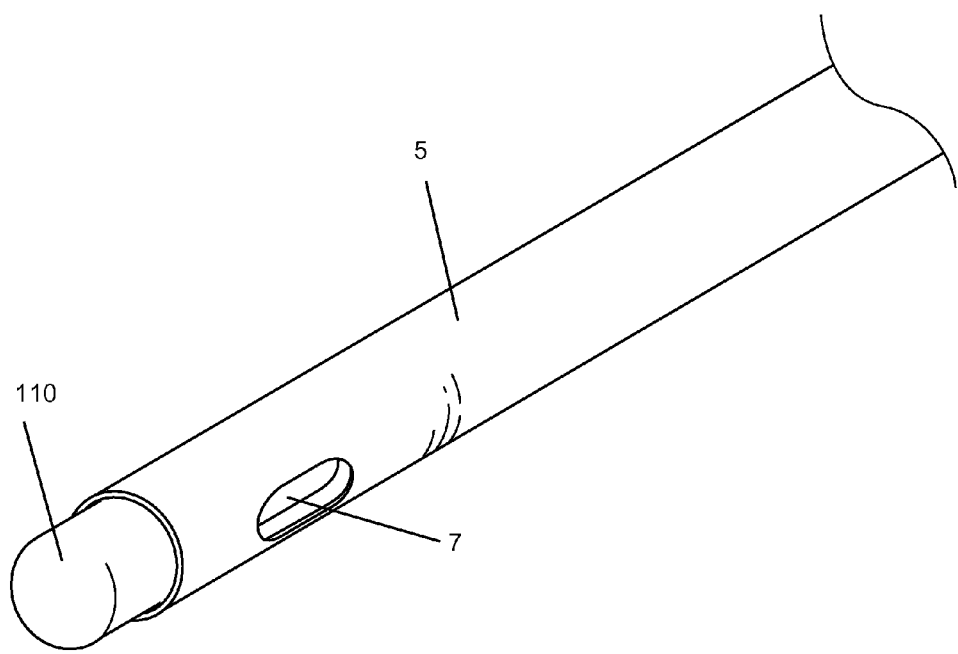
FIGS. 2A-2D illustrate various views of an alternate embodiment of an apparatus for creating a channel through a foreign material in accordance with the present invention.
Figure 2B:
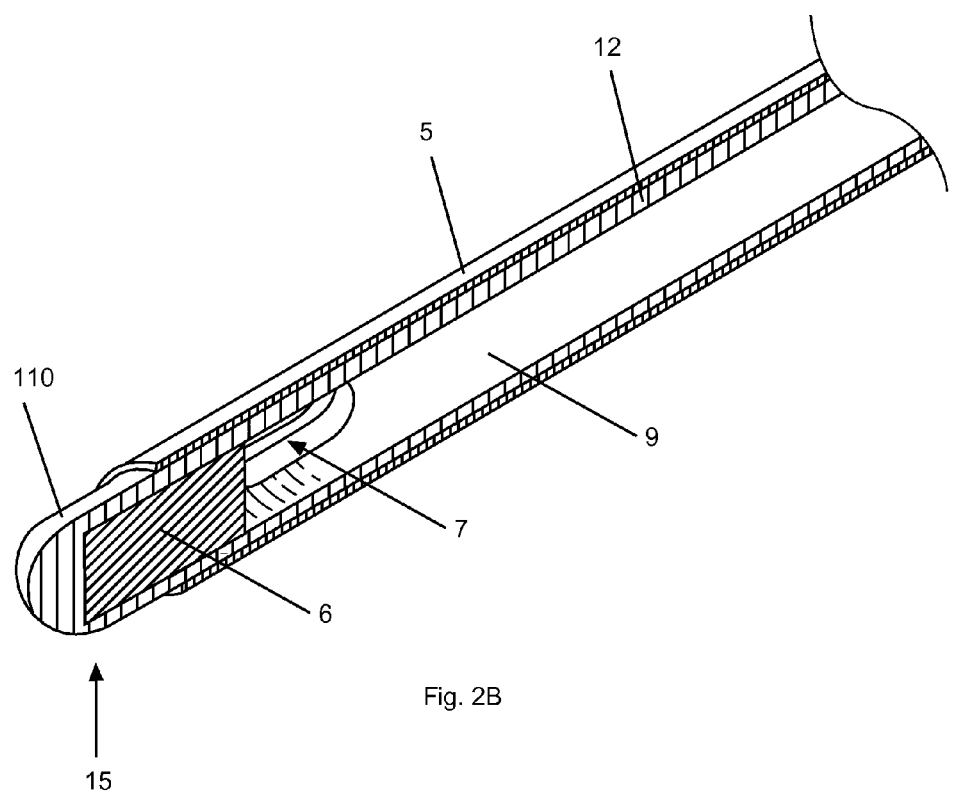
Figure 2C:
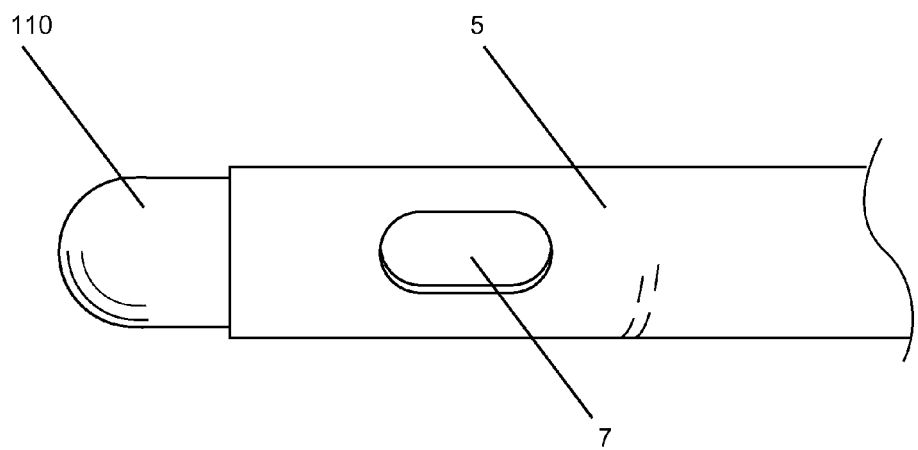
Figure 2D:
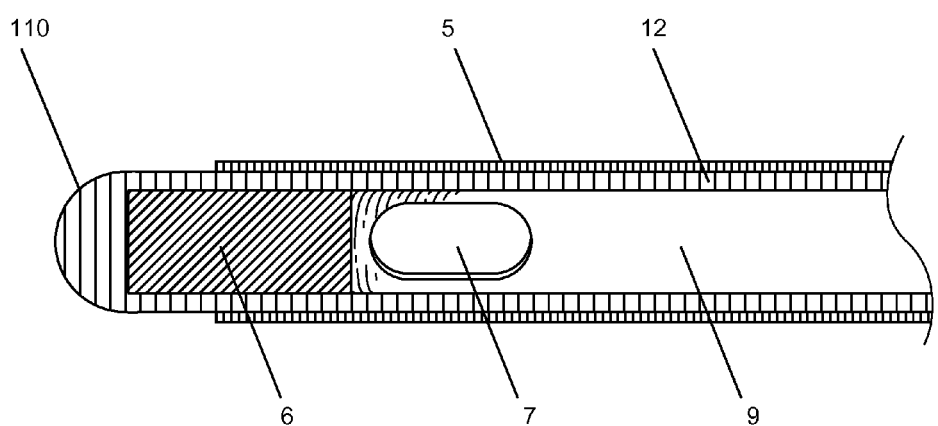

Additional details regarding the apparatus described in FIGS. 1-2D and method that may be employed therewith that are not mentioned herein may be found in U.S. application Ser. No. 11/905,447, filed Oct. 1, 2007, (now U.S. Pat. No. 8,192,425) and U.S. application Ser. No. 13/468,939, filed May 10, 2012. Further details regarding the device may additionally be found in U.S. provisional application Ser. No. 60/884,285, filed Jan. 10, 2007, and provisional application Ser. No. 61/653,697 filed May 31, 2012. The contents of all above-named applications and patents are incorporated herein by reference in their entirety.

Figure 3A:
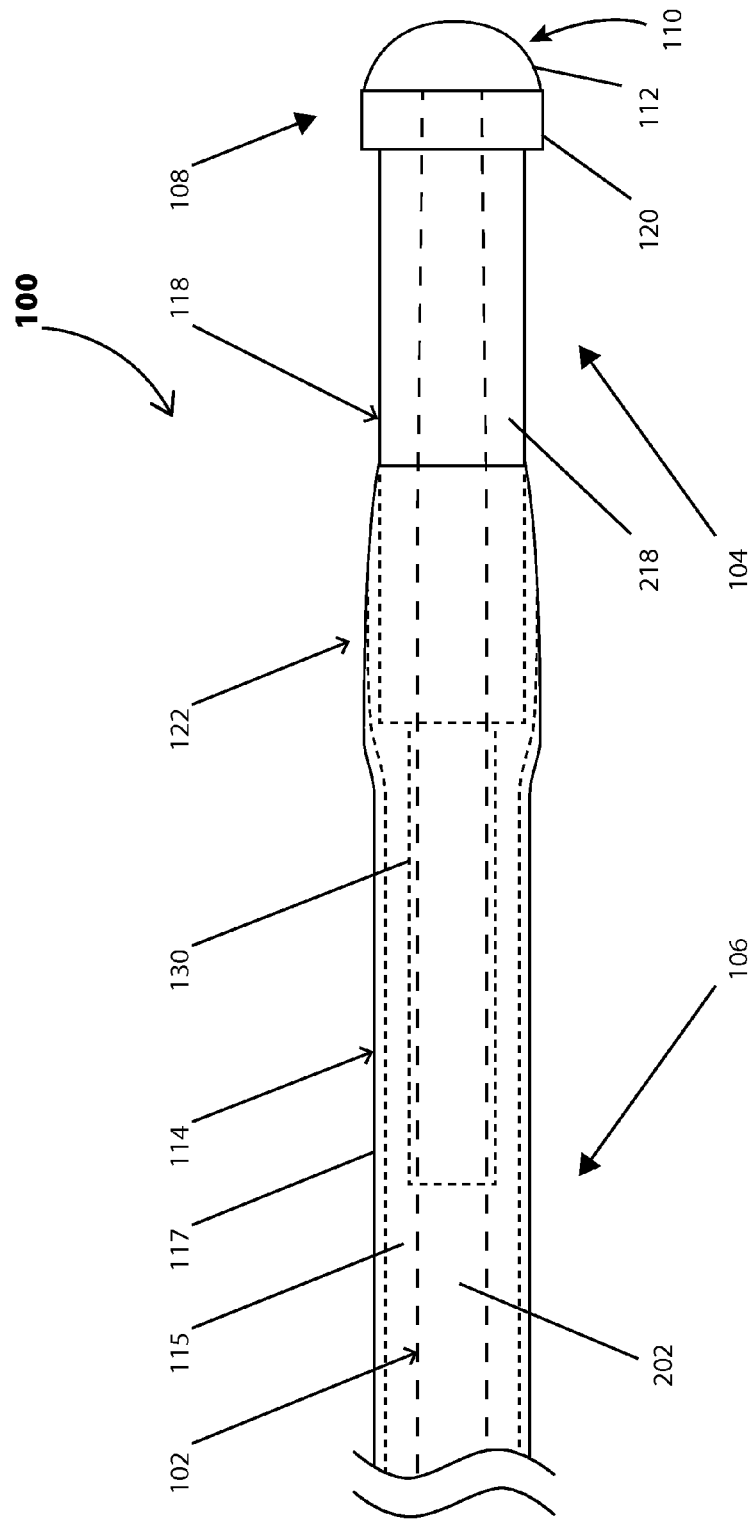
FIGS. 3A-3B show various view of an apparatus for creating a channel through a foreign material in accordance with an alternate embodiment of the present invention.
Figure 3B:
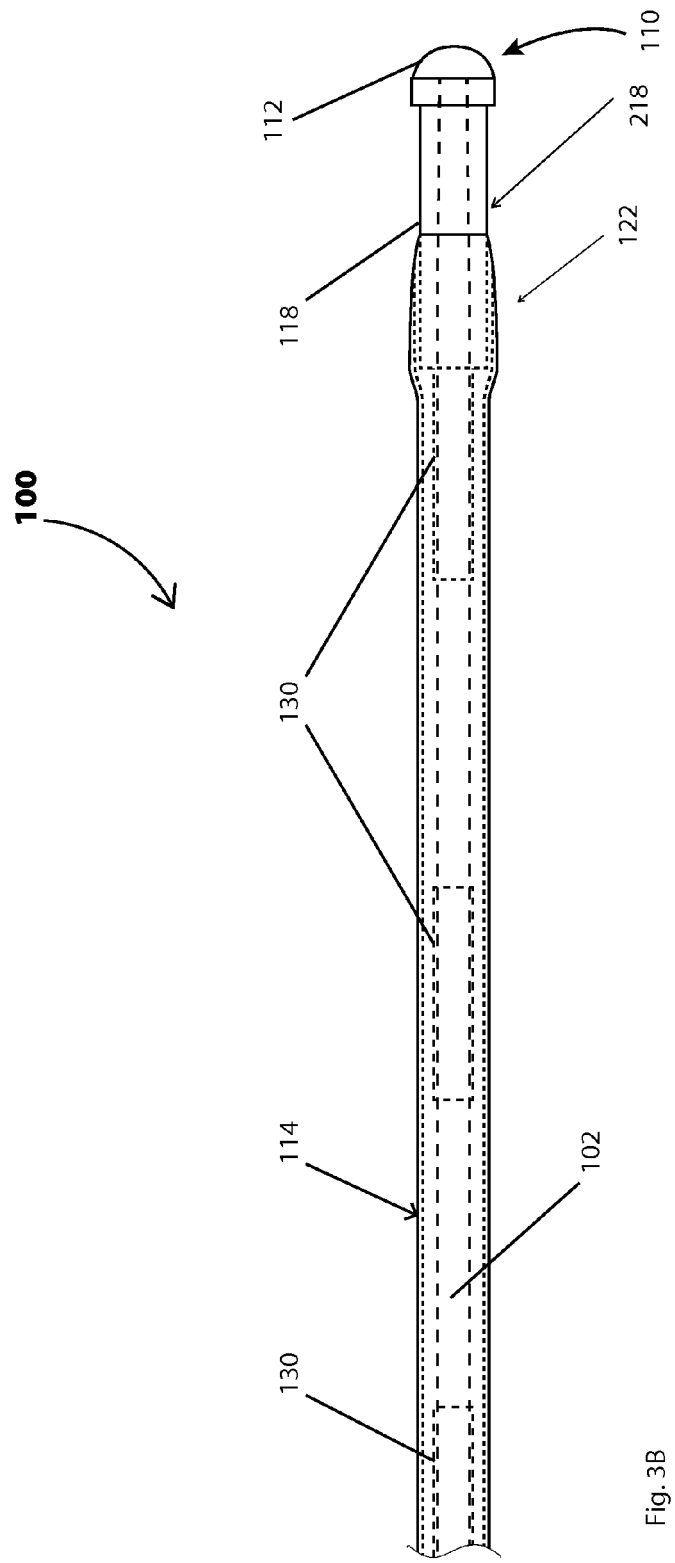

In another specific example, the apparatus 100 in accordance with an embodiment of the present invention, is a PowerWire™ Radiofrequency Guidewire that is also available from Baylis Medical Company Inc. The PowerWire™ Radiofrequency Guidewire is usable with a BMC Radiofrequency Puncture Generator (e.g. model RFP-100) and the BMC Connector Cable (e.g. model RFP-101), also available from Baylis Medical Company Inc. The PowerWire™ Radiofrequency Guidewire is operable to deliver radiofrequency energy to create the channel within the foreign material. The PowerWire™ Radiofrequency Guidewire is particularly useful for positioning and guidance in peripheral vasculature. The PowerWire™ Guidewire is a relatively flexible device which allows it to be maneuvered within vasculature with relative ease, allowing it to be positioned at a desired location for example within the vasculature. The flexibility of the guidewire allows it to be guided and advanced through tortuous anatomy to allow it be positioned at a desired target location adjacent foreign material positioned within the body to allow it to create a channel therethrough. More particularly, the PowerWire™ Radiofrequency Guidewire may be used to create a channel through foreign material within a stent-graft that may be positioned within a body vessel, for example as discussed with reference to FIGS. 6A-9B herein below. Some embodiments of the Power-Wire™ Radiofrequency Guidewire are shown in FIGS. 3A-3B. In general, an apparatus 100, as shown in FIG. 3A, comprises an inner elongate member 102 which is an electrical conductor. In one embodiment, the inner elongate member 102 comprises a core wire 202. In one example, the core wire 202 may comprise a shape memory alloy, such as a nickel-titanium alloy, such as Nitinol™. The elongate member has an insulation layer 114 disposed along a portion thereof including along a proximal region 106 of the device.

As shown in FIG. 3A, the apparatus or electrosurgical device 100 further defines a distal region 104 having a heat shield 118 disposed at or near the distal end of the core wire 202 substantially distal to the insulation layer 114. The heat shield 118 may alternatively be referred to as a thermal shield or a heat sink. An electrode tip 112 is coupled to the distal end of the elongate member 102 distal to the heat shield 118 at the distal tip 108. The distal tip 108 defines the part of the distal region 104 that is distal to the heat sink or heat shield 118. In some embodiments, a support structure 120 is positioned distal to the heat shield 118 for supporting the electrode tip 112. As such, the heat shield 118 is positioned between the insulation layer 114 and the energy delivery component, such as electrode tip 112 positioned at the distal end of core wire 202. The electrode tip 112 forms an energy delivery component or electrode 110.

In some embodiments, the support structure 120 provides a distal surface on which the electrode tip 112 is positioned and/or formed. In one such embodiment, in order to create a dome shaped electrode tip 112 a welding process is used to melt a distal most portion of wire 202 to form a segment of sphere for e.g. a hemispherical shape. In one specific example, a laser welding process is used and the support structure 120 provides a substantially planar distal face onto which the domed shaped electrode tip 112 is formed. In one specific example, the support structure 120 comprises a metal such as Tantalum and the core wire 202 comprises Nitinol. When the Nitinol core wire 202 is laser welded it fuses with the Tantalum support structure 120 at the interface between the two materials. An integral bond is formed at the boundary between the Nitinol electrode tip 112 and the tantalum support structure 120.

In some embodiments, the support structure 120 may comprise materials such as tantalum, iridium, gold or stainless steel. In one example, the support structure 120 is radiopaque and provides the physician with a visual indication of the location of the electrode tip 112 under imaging. This helps determine the location of electrode tip 112 within the patient's body during use. In one specific example, an annular tubular structure comprising radiopaque tantalum metal is used as the support structure 120. The support structure 120 is threaded onto the distal end of the core wire 202 and the electrode tip 112 is positioned or formed distal to and adjacent to the support structure 120, the support structure 120 being positioned distal to heat shield 118. In one specific embodiment, the tantalum support structure 120 has an inner diameter of about 0.279 mm, an outer diameter of about 0.812 mm, and has a longitudinal length of about 0.254 mm. In one embodiment, the support structure 120 is electrically conductive and forms a part of the electrode 110. Thus, the support structure 120 together with the electrode tip 112 forms the energy delivery component or electrode 110. In one such example, the electrode 110 comprises a Nitinol electrode tip 112 is formed on a tantalum support structure 120 that is positioned distal to the heat shield 118.

As outlined previously, the elongate member has an insulation layer 114 disposed along a portion thereof including along a proximal region 106 of the device. The insulation layer 114 may help to electrically insulate a portion of the electrosurgical device or apparatus 100. This may help protect the patient and the user for e.g. the physician from electrical current during use of device 100. A variety of materials may be used for the insulation layer 114, including but not limited to polymer or ceramic. A polymer insulation layer 114 may be provided using a heat shrink process or a melt processing method. Alternatively any other suitable method may be used. In some embodiments, the insulation layer 114 may be provided through a dip coating process. In one embodiment, a polymer combination may be used for the insulation layer 114. As an example, a two layer heat shrink layer may be used comprising an inner polymer layer 115 and an outer polymer layer 117. In a specific instance of this example, the insulation layer 114 comprises a combination of FEP and PTFE polymers, where the inner polymer layer 115 comprises FEP and the outer polymer layer 117 comprise PTFE as shown in FIG. 1A. A process combining re-flow and heat-shrink is used and the dual polymer layer is heated to a temperature of about 660° F., allowing the inner FEP layer to flow around and encapsulate the one or more platinum bands 130 disposed on core wire 202. Whereas, the outer PTFE layer recovers to a pre-specified diameter around the FEP and provides a smooth outer finish. In one embodiment of the present invention, a portion of the electrosurgical device 100 may have a hydrophilic coating disposed thereon. In a non-limiting example, the hydrophilic coating may comprise Hyaluronic Acid (HA).

In the embodiment illustrated in FIGS. 3A and 3B, a junction 122 forms between the insulation layer 114 and the heat shield 118. In the example shown, the insulation layer 114 extends over or overlaps the ceramic heat shield 218 at the junction 122 to provide a seamless transition and a sealed junction. In one specific example, the insulation layer overlaps the proximal portion of the ceramic heat shield 218 by about 1 mm. This overlap helps to limit the arcing to the electrode tip 112 at the distal tip 108. Thus the overlap may help minimize arcing observed behind the heat shield near the junction 122 and may help minimize degradation of the insulation layer 114 from the heat generated at the electrode tip 112 from the delivery of electrical energy through the electrode tip 112. In another embodiment, the insulation layer 114 and the heat shield 118 such as ceramic heat shield 218 may be flush against one another (or in other words may abut one another) to form a junction there-between. In still another embodiment, a step-down heat shield may be used.

In one embodiment, as shown in FIG. 3B multiple radiopaque bands 130 are positioned on the core wire 202. These provide reference markings which when viewed under imaging provide guidance to the physician for positioning the apparatus 100 within a patient's body and/or advancement of the apparatus 100 during use. The radiopaque bands 130 may comprise materials such as platinum, iridium, gold, silver, tantalum and tungsten or their alloys, or radiopaque polymer compounds. In one example, as mentioned above, platinum is used for the radiopaque bands 130. In one example, the radiopaque band 130 is secured to the core wire 202 to retain/support the heat shield 118 in position. In one specific instance of this example, the radiopaque band 130 is spot welded to the core wire 202. In another example, the heat shield 118 is retained/supported in place by the core wire 202. The core wire 202 has wider sections adjacent and proximal to the distal section. The heat shield 118 is loaded on the distal section and retained by this wider section of the core wire 202.

In some embodiments of the present invention, the heat shield 118 is provided as an electrical and thermal insulator that functions to insulate and thus protect the device proximal region 106 from the heat generated at the electrode tip 112 and functions to prevent arcing between the electrode tip and the device proximal region 106. The device proximal region is the portion of the device that is proximal to the heat shield 118. In some embodiments, the heat shield 118 has a thermal conductivity that allows the heat shield 118 to dissipate heat by effectively conducting heat away from the electrode tip 112. This may prevent the heat shield 118 from cracking. Thus, the heat shield 118 electrically and thermally protects the device proximal region 106 and thus the insulation layer 114 in the device proximal region 106. In some embodiments, the heat shield 118 may have a thermal conductivity k that is greater than about 1 Watt/m·K (1 watt per meter kelvin). In other embodiments, the thermal conductivity k of the heat shield 118 may be greater than about 2 Watts/m·K (2 watts per meter kelvin).

In some embodiments the heat shield 118 may comprise glass or alternatively may comprise a ceramic heat shield 218. The ceramic heat shield 218 may comprise materials such as alumina, aluminum oxide, zirconia toughened alumina (ZTA) or zirconium oxide. In other embodiments, other ceramics such as Silicon Nitride or Silicon carbide may be used. In still other embodiments, any other suitable ceramic may be used to form the ceramic heat shield 218. In one particular example, the ceramic heat 218 is made of pure alumina or sapphire crystal comprising a single/mono crystal aluminum oxide. In one such example, as shown in FIG. 3A, the ceramic heat shield 218 comprises a tubular cylinder having a longitudinal length of about 2.54 mm. The tubular cylindrical ceramic has an inner diameter of about 0.292 mm and an outer diameter of about 0.660 mm. In some such embodiments, the heat shield 118 may comprise material that can be viewed under an imaging modality. In one particular example, the ceramic heat shield 218 is radiopaque.

Additional details regarding the apparatus shown and described in FIGS. 3A-3B, and methods of use thereof not mentioned herein may be found in U.S. application Ser. No. 11/926,292, filed on Nov. 8, 2010, and U.S. patent application Ser. No. 11/520,754, filed on Sep. 14, 2006, (Now U.S. Pat. No. 7,828,796). Further details regarding the device may additionally be found in U.S. provisional patent application Ser. No. 60/596,297, filed Sep. 14, 2005. All of these US patent applications and provisional patent application are hereby incorporated by reference in their entirety.

In some embodiments of the present invention, the apparatus 100 further comprises one or more means for guiding the apparatus 100 within the body of the patient. For example, in one particular embodiment, the apparatus 100 further comprises an ultrasound transducer (not shown in the drawings) associated with the distal end region 104. The ultrasound transducer (not shown in the drawings) may be operable as an intra-vascular ultrasound (IVUS) device, which may assist in determining the position of the apparatus 100 within a blood vessel, for example. In such an embodiment, the ultrasound transducer (not shown in the drawings) may be electrically connected to an ultrasound generator, for example via one or both of the elongated member 102. In another specific embodiment, the apparatus 100 further comprises at least one optical fiber (not shown in the drawings) which may be optically coupled to an optical coherence reflectometry (OCR) system (not shown in the drawings), which may also assist in determining the position of the apparatus 100 within a blood vessel, for example. Another example of a suitable device or apparatus is described in application Ser. No. 12/926,292, which is incorporated herein by reference in its entirety. In further embodiments, a steering or articulating device may be used to guide the apparatus to the foreign material.

Method

In some embodiments, the apparatus 100 is usable to create a channel in a foreign material located in the body of a patient (not shown in the drawings). This channel may be created, in some embodiments, at least partially by the delivery of energy using the electrode 110. More specifically, the electrode 110 is energized with a radiofrequency current and the electrode 110 is then used to deliver energy into the foreign material to create the channel. In some embodiments, the energy delivered in the foreign material is thermal energy.

Without being limited to a particular theory of operation, it is hypothesized that, in some embodiments, the proposed method is performed when the electrode 110, which is energized with a radiofrequency current, heats up to a predetermined temperature. For example, the predetermined temperature may be substantially larger than a melting temperature of the foreign material. Then, thermal energy is transferred from the electrode 110 to the foreign material to substantially melt the foreign material adjacent to the electrode 110, thereby creating a channel through the foreign material. In other embodiments, it is hypothesized that water may be absorbed by the foreign material, and radiofrequency energy that is thereafter delivered to the foreign material may cause vaporization of the water adjacent to the electrode 110, thereby creating a channel through the foreign material.

In some embodiments, heating of the electrode 110 is performed while the electrode 110 is positioned at a predetermined distance from the foreign material and from biological tissues adjacent to the foreign material. Positioning the electrode at a predetermined distance from the foreign material and from the biological tissues adjacent to the foreign material minimizes risks of injuring the biological tissues adjacent to the foreign material. For example, the predetermined distance is such that thermal energy transfer between the electrode 110 and either or both of the foreign material and biological tissues adjacent to the foreign material results in a non-damaging increase in temperature thereof. As mentioned hereinabove, the use of a radiofrequency current to heat the electrode 110 helps in minimizing this heat transfer, and therefore contributes to the practicality of the proposed method as the predetermined distance is then relatively small.

Minimizing injuries to tissues is of paramount importance when performing interventions in patients. Indeed, injuring a tissue typically creates stress and inflammatory responses that may cause irreversible damages to many tissues. In addition, many patients have a relatively sensitive hypothalamic-pituitary-adrenal axis (HPA axis) and local stresses to tissues can lead in these patients to systemic and psychiatric conditions and diseases. In some embodiments, the proposed method is performed in the heart of the patient. In these cases, these irreversible damages can lead to dysfunctions in the contractile and electrical conductivity properties of the cardiac tissue, which themselves can lead to life-threatening conditions.

It is hypothesized that providing the radiofrequency current to the electrode 110 within the body creates a layer of water vapor around the electrode 110, which reduces thermal transfer between the electrode 110 and adjacent structures that are sufficiently spaced apart therefrom. This helps in ensuring a relatively fast heating of the electrode 110 and reduce risks of damaging biological tissues as described hereinabove.

In such embodiments, the electrode 110 is then moved so as to be substantially adjacent to the foreign material. As the electrode has now attained a temperature substantially higher than the melting temperature of the foreign material, the electrode effectively melts the foreign material to create a channel therethrough.

However, in alternative embodiments of the invention, positioning of the electrode 110 substantially adjacent to the foreign material, for example to a first surface of the foreign material, is performed before energizing the electrode 110.

Generally speaking, the aforementioned specifics of the proposed method are typically part of a treatment procedure comprising the steps of: providing an apparatus 100, or any other suitable apparatus; inserting at least a portion of the apparatus 100 into the body of the patient, for example by introducing the distal end region into the body of the patient; positioning the electrode 110 substantially adjacent to the material first surface; energizing the electrode 110 with a radiofrequency current; and using the electrode 110 energized with the radiofrequency current to deliver energy into the foreign material to create the channel. Further embodiments may comprise additional steps of, for example, manipulating an actuator, or otherwise guiding the apparatus 100 through one or more of the body vasculature of the patient and the channel.

In accordance with embodiments of the treatment method aspects of the present invention, the apparatus 100 may be a component of a system including an energy source (not shown in the drawings) (such as, for example, the RFP-100, RFP 100A or RFP-200 Baylis Medical RF Puncture Generators, manufactured by Baylis Medical Company Inc., Montreal, Canada), and a grounding pad (not shown in the drawings) or any other return electrode, if operated in a monopolar mode.

Figure 4:
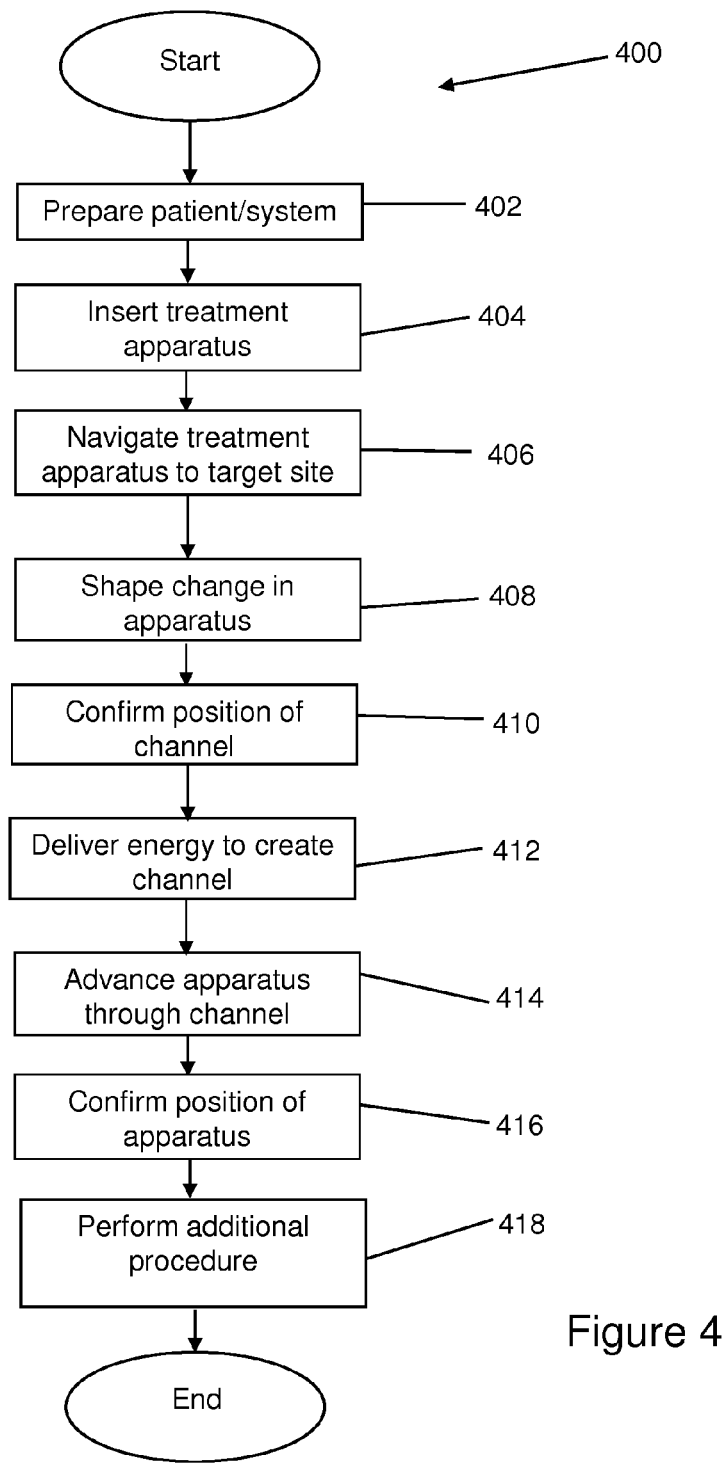
FIG. 4, in a flow chart, illustrates a method for creating a channel in a foreign material in accordance with an embodiment of the present invention.

FIG. 4 illustrates, in a flow-chart form, one embodiment of a method 400 in accordance with the present invention. This embodiment comprises: at step 402, preparing a patient and a system for treatment; at step 404, inserting a portion of the apparatus 100 into the body vasculature of the patient; at step 406, navigating the apparatus 100 through the body vasculature to a target site; at step 408, changing a of shape, or otherwise reorienting the apparatus 100 in order to position the electrode 110, or any other suitable electrode, adjacent at least a portion of the foreign material; at step 410, confirming or otherwise assessing the position of the electrode 110; at step 412, delivering energy via the apparatus 100 to create a channel in the foreign material; at step 414, advancing the apparatus 100, for example the distal end region 104 and the electrode 110, through the channel; at step 416, assessing the position of the electrode 110 or any other portion of the apparatus 100 after it has been advanced through the channel; and, at step 418, performing an additional procedure at or around the target site. The reader skilled in the art will readily appreciate that the patient may be a human or an animal and that one or more of these steps may not necessarily be performed in a given procedure or that one or more of these steps may be performed in a different order, as will be further clarified hereinbelow.

In step 402, preparing a patient for treatment may include, but is not limited to one or more of: visualizing one or more treatment sites within the body of the patient using fluoroscopy, x-ray, contrast media, labeled markers such as radioactive compounds or solutions, using endoscopy procedures, using ultrasound, using Doppler imaging, or any other visualization method; characterizing the vascular system of the patient by measuring blood or serum levels of various compounds; measuring vascular pressure; and undertaking any other measuring or monitoring technique that may provide information that may be useful during any other step of the method. In step 402, preparing a system for treatment may include, but is not limited to one or more of: connecting a treatment apparatus, for example the apparatus 100 as described above, to an energy source; connecting a grounding pad or other return electrode to the energy source; placing the grounding pad or return electrode on the body of the patient; and attaching one or more additional components to the apparatus 100. As mentioned above, one or more of these steps may not be performed in a particular procedure, depending on the apparatus 100 being used and the specific procedure being performed.

The step 404 of inserting the apparatus 100 into the body vasculature of the patient may comprise percutaneously inserting the apparatus 100 into a blood vessel of the body vasculature through which the apparatus may be navigated to the target site. For example, in some embodiments, the apparatus 100 may be inserted into a femoral artery or vein or a subclavian artery or vein. The apparatus may be inserted directly into the blood vessel or may be inserted through a guiding catheter or sheath.

The step 406 of navigating the apparatus 100 through the body vasculature to a target site may involve advancing the apparatus 100 through the body vasculature to the target site. In some specific embodiments, in which the apparatus is inserted through a guiding sheath or catheter, the sheath or catheter may initially be navigated to the target site, for example by initially inserting a guidewire to the target site and then tracking the sheath/catheter over the guidewire. Once the sheath/catheter is in place, the guidewire may be removed and the apparatus 100 may be inserted through the sheath/catheter. Step 406 may additionally involve any of a variety of visualization techniques, including those techniques mentioned above for visualizing one or more treatment sites within the body of the patient. In one embodiment, the apparatus 100 may be furnished with one or more radiopaque markers, which may aid in the visualization of the apparatus 100.

The step 408 of affecting a change of shape in the apparatus 100 may be required, for example if the step of navigating the apparatus 100 does not position the apparatus 100 sufficiently precisely. This step is, in some embodiments, accomplished by effecting a change of shape in the distal end region of the apparatus 100, as described hereinabove. In some embodiments, it may be desirable to approach the foreign material substantially perpendicularly, for example at an angle of about 80 degrees to about 100 degrees, and step 408 is usable to control this angle.

The step 410 of confirming a position of the apparatus 100 may involve visualizing the position of one or more portions of the apparatus 100 within the body of the patient. For example, radiopaque markers included in the apparatus 100 may be visualized using fluoroscopy. Alternatively, or in addition, radiopaque contrast may be injected, for example through the guiding sheath/catheter, in order to confirm the position of the apparatus 100. Furthermore, in some embodiments, the apparatus 100 may include a pressure sensor (not shown in the drawings) operatively coupled to the distal end region of the apparatus for measuring a pressure at or around the distal end of the apparatus. In such embodiments, blood pressure may be reassured in order to confirm the position of the apparatus.

The step 412 of delivering energy may include an optional step of measuring, assessing or sensing the composition of the foreign material to be penetrated. For example, in one embodiment, the apparatus 100 may be used as part of an impedance monitor to determine the impedance of the material to be penetrated. The impedance value thus measured may then be compared to known impedance values of various materials in order to determine the composition of the material to be penetrated. Then, energizing the electrode 110 is performed, in some embodiments, at least in part, in a manner depending on the composition of the foreign material. For example, the electrode 110 may be energized at various power levels, depending on the nature of the foreign material. Alternatively, a change in impedance may indicate that the material in contact with the apparatus has changed. For example, a lower impedance may indicate that the apparatus is in contact with a metallic or otherwise conductive portion of a stent, scaffold, or septal occluder, as opposed to the graft material associated with the stent/scaffold/occluder. In such a situation, a user may reposition the apparatus until a suitable impedance measurement is recorded indicating that the apparatus is positioned away/at a distance from the metallic material/portion, and may be substantially adjacent to the foreign material through which the channel is to be created.

Alternatively, tactile feedback may be used to assist in determining the material in contact with the apparatus. For example, a user may use tactile feedback to determine whether the apparatus is in contact with metallic material of a stent/scaffold or more flexible graft material, through which a channel may be created. Alternatively, or in addition, imaging techniques (for example OCR and/or IVUS) may be used to determine the composition of material in contact with the apparatus 100. As described hereinabove, the composition of the material to be penetrated may determine the initial parameters of energy delivery.

The step 412 of delivering energy via the apparatus 100 to create a channel in the foreign material comprises, in one embodiment, delivering electromagnetic energy (for example electric energy in the radiofrequency (RF) range) to the electrode 110. In one specific embodiment, the RF current provided may have a frequency in the range of from about 300 kHz to about 1 MHz, and more specifically, in very specific embodiments of the invention, of from about 460 kHz to about 500 kHz, and may be delivered with a power of at least about 5 W at a voltage of at least about 75 Volts (peak-to-peak).

In some embodiments, one or more parameters may be measured substantially while energy is being delivered and/or the device is being advanced. For example, impedance may be measured substantially continuously or at predetermined intervals during energy delivery and/or advancement of the apparatus and a change in impedance may lead to a change in energy delivery. In one particular example, a drop in impedance may indicate that the apparatus is contacting a metallic portion of a stent/scaffold/occluder and energy delivery may be stopped so that the device may be repositioned. The change in energy delivery may be automatic or may be manually performed by the user.

In some embodiments of the invention, the energy may be delivered for a predetermined amount of time before stopping the delivery of the energy. In other embodiments, the intended user may decide, during the course of the procedure, on the amount of time during which energy should be delivered. The intended user's decision may depend, for example, on one or more of tactile feedback, impedance measurements, pressure measurements, predetermined information regarding the material being penetrated (e.g. the thickness of the material) or the preferences of the intended user. In one example, if a user feels that the device has penetrated through the foreign material he may stop delivering energy. In some embodiments, the amount of time during which energy is delivered is from about 0.1 seconds to about 5 seconds. In a more specific embodiment of the invention, the amount of time during which energy is delivered is from about 1 second to about 2 seconds. During these periods of time, the energy may be delivered continuously or as a pulsed waveform.

The step 414 of advancing the apparatus through the channel may comprise applying a longitudinal force to the proximal end region 106 of the apparatus 100 in order to advance the distal end region 104 of the apparatus 100 through the channel. Alternatively, mechanical or magnetic means for advancing the apparatus may be used. In some embodiments, step 414 occurs at least partially concurrently with step 412, such that the apparatus is advanced while energy is being delivered.

Following step 414, the position of the apparatus 100, after passing through the channel, may be confirmed at step 416. Step 416 may be performed in substantially the same manner as step 410, described hereinabove.

The step 418 of performing another treatment procedure may involve, in some embodiments, one or more of: introducing a balloon catheter, a dilator or other means for dilation of the channel, to the target site, for example overtop of or through the apparatus 100; introducing a stent or other supporting structure to the target site, for example overtop of or through the apparatus 100; delivering a pharmaceutical compound to the target site; delivering energy to create a lesion or coagulate tissue or fluid in the vicinity of the target site; introducing embolic coils; placing an IVUS or OCR probe for visualization; or adding or removing any other material to or from the site. In addition, this step may further comprise removal and possible re-attachment of a handle or connector of the apparatus 100, in order to allow for the introduction of another device to the treatment site. As mentioned hereinabove, in alternative embodiments of the invention, the electrode 110 is energized after having been positioned adjacent to the foreign material.

Embodiments of the treatment procedure described above may be particularly useful to create a channel through material of a stent graft occluding one or more vessels of a patient's body. Several examples of such applications are noted hereinbelow. While these examples have been described in specific detail, one of skill in the art will appreciate that embodiments of the present invention may be utilized in various other procedures and applications.

EXAMPLES

Application 1-Cardiac Septal Procedures

Example 1A

In a first example, an embodiment of a proposed method is used to create a channel 512, seen in FIG. 5B, within a septal patch 510 made of foreign material, the septal patch 510 defining a material first surface 514 and a substantially opposed material second surface 516. The channel 512 extends between the material first and second surfaces 514 and 516. The septal patch 510 extends across an aperture 518 defined by the septum 520 of the heart 500 of the patient, for example an atrial septum or a ventricular septum. For example, the septal patch 510 covers the aperture and extends in a plane outside of the septum 520. In other examples, the septal patch 510 extends inside the aperture 518. Some of these procedures may involve patients that have had a septal defect repaired with the septal patch 510. In some cases, such patients may suffer from one or more conditions which require access to the left side of the heart for treatment to be performed. In such situations, access to the left side of the heart may be gained by creating the channel 512 in the septal patch 510. In such embodiments, the septal patch 510 may be made of a foreign material selected from the group consisting of polyethylene terephthalate (PET, for example Dacron®), cotton, a polyester material and fabrics thereof.

With reference to FIG. 5A, the apparatus 100 is inserted through the inferior vena cava 502 into the right atrium 506 of the heart 500. In alternative embodiments, access to the right atrium may be achieved via the superior vena cava 504 as described, for example, in U.S. patent application Ser. No. 11/265,304 (Filed on Nov. 3, 2005), now U.S. Pat. No. 7,947, 040, which is incorporated herein by reference in its entirety. FIG. 5A shows the apparatus 100 positioned in the right atrium 506 with the electrode 110 located substantially adjacent the material first surface 514. FIG. 5B shows the apparatus 100 positioned in the left atrium 508 after being advanced through the channel 512. In this particular embodiment, radiofrequency energy may be delivered, for example, at about 5 W for a period of less than about 5 seconds.

Example 1B

Figure 5C:
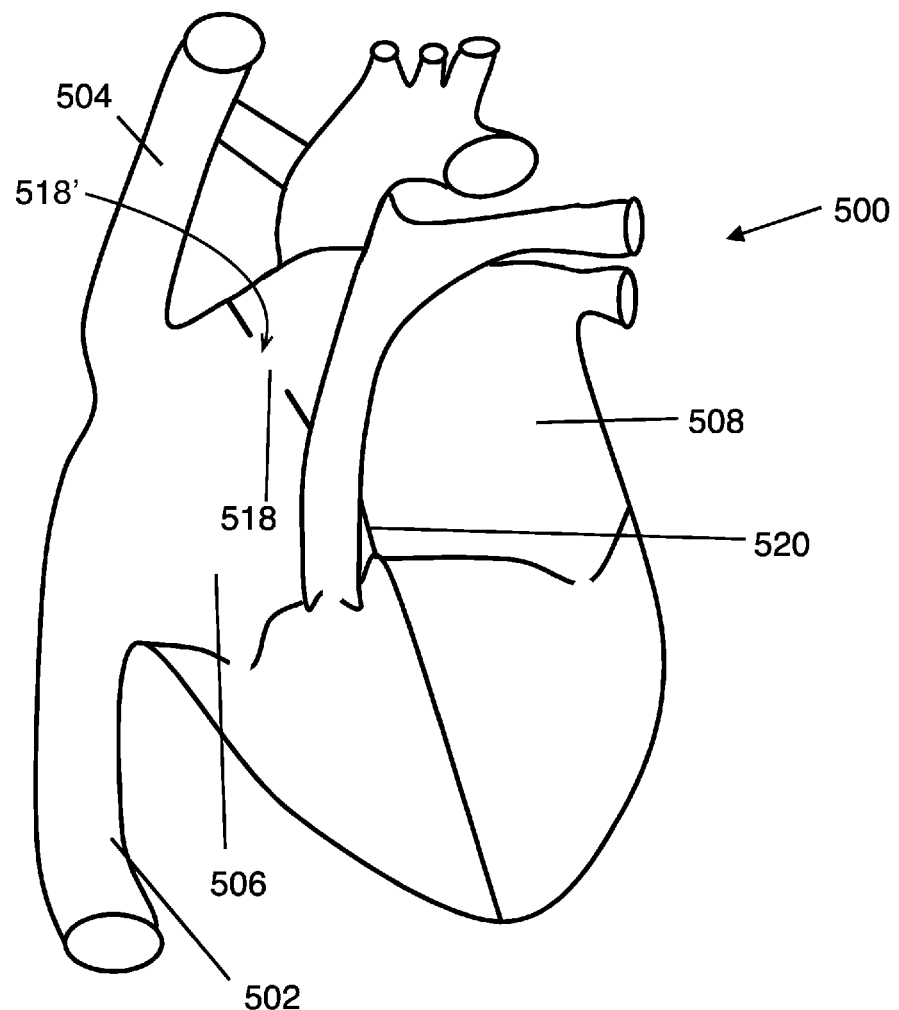
FIG. 5C, in a schematic view, illustrates a septal defect in the form of an aperture formed in the heart of a patient.
Figure 5D:
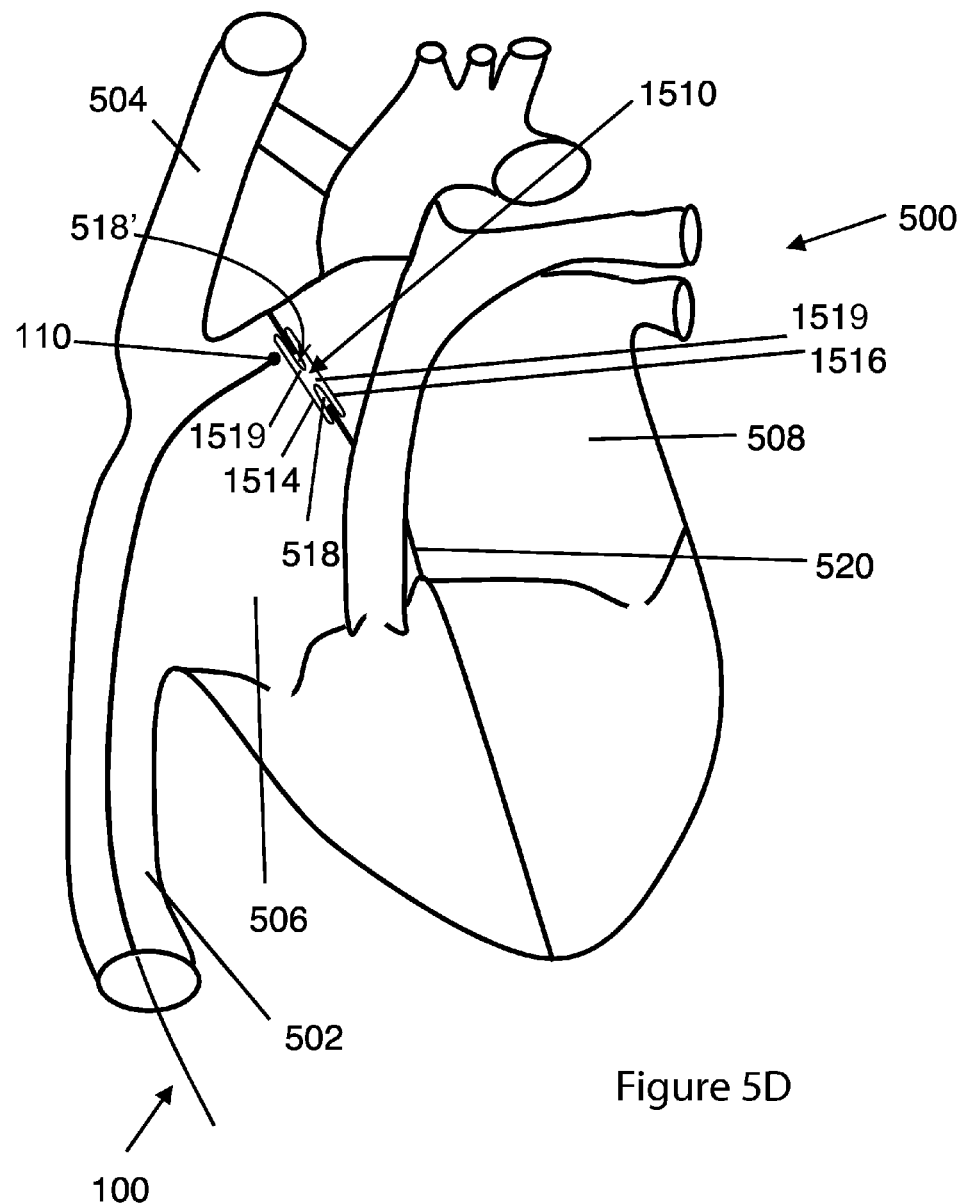
FIG. 5D, in a schematic view, illustrates one of more steps of a method for creating a channel in an occluder extending across an aperture formed in the heart of a patient in accordance with an embodiment of the present invention.

In another example, with reference to FIGS. 5C-5I, an embodiment of a proposed method is used in a procedure to create a channel within foreign material that is positioned within a patient's body. More specifically, the proposed method may be performed in patients that have a septal defect 518' within the septum 520 of the heart 500 (as shown more clearly in FIG. 5C), where the septal defect 518' has been previously repaired with foreign material. For example, the foreign material may be included within an occluder 1510 positioned within the septum 520, as shown in FIG. 5D. The septal occluder 1510 prevents blood from shunting between the left side and the right side of the heart 500 that occurs when the septal defect 518' is present. For example, the septal defect 518' may be in the form of an aperture 518 within the septum 520 of the heart 500, for example within an atrial septum as shown. Alternatively, the defect may be within the ventricular septum. The occluder 1510 may be positioned within the septum 520 such that it extends across the aperture 518 to repair the septal defect 518'. However, some such patients that have had a septal defect 518' repaired with an occluder 1510, may additionally suffer from one or more conditions which require access to the left side of the heart 500 for treatment to be performed. In these patients access is required form the right side of the heart 500 to the left side of the heart 500 through the septum 520. For example where an atrial septal defect 518' has been treated, access may be required from the right atrium 506 into the left atrium 508 across the septal occluder 1510 that is positioned within the septum 520. However, the presence of the septal occluder 1510 may create a challenge for traversing there-through using mechanical means. Thus, in accordance with an embodiment of the present invention, a method and apparatus 100 are provided for facilitating access to the left side of the heart 500 by creating a channel 1512 within the occluder 1510 using radiofrequency energy, as discussed further herein below.

Figure 5E:
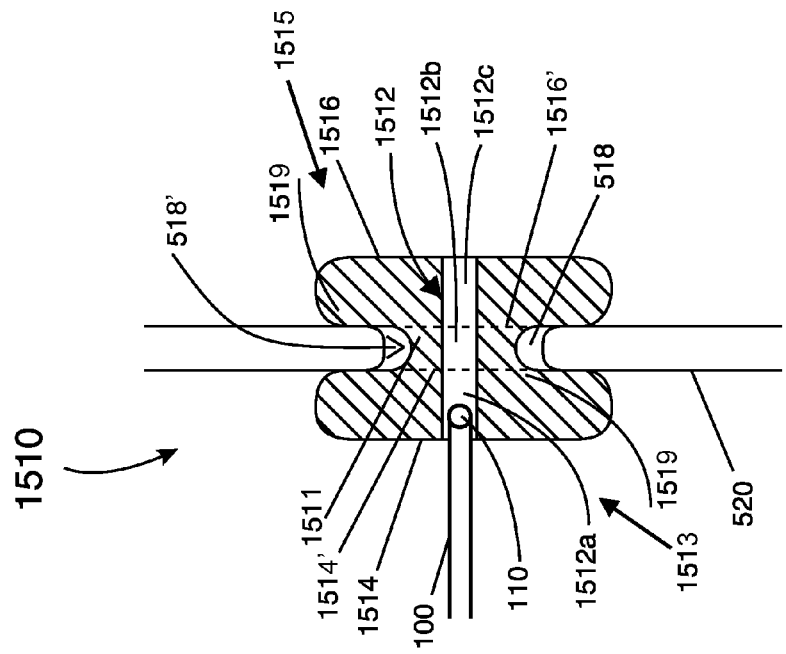
FIGS. 5E and 5F are cross-sectional views showing one of more steps of a method for creating a channel in an occluder extending across an aperture formed in the heart of a patient in accordance with an embodiment of the present invention.
Figure 5F:
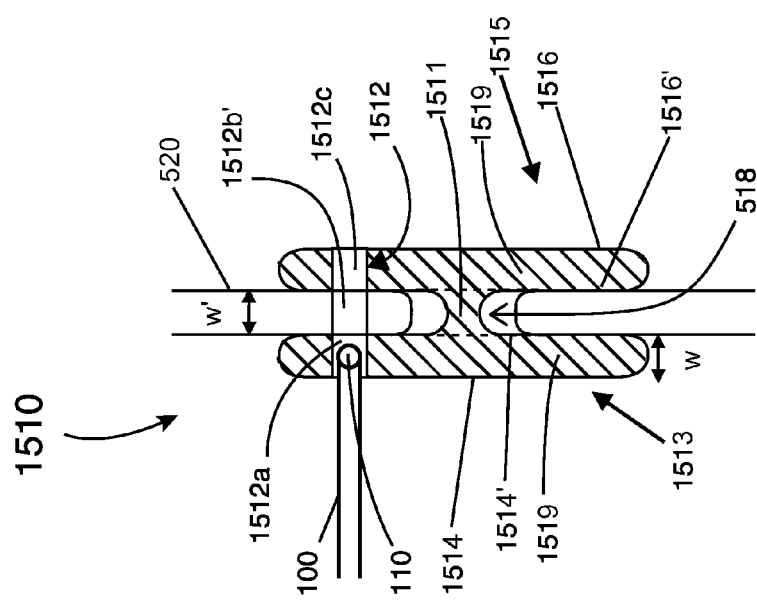

The method of the present invention may be used to traverse through various occluders 1510 as may be known in the art. In some embodiments the occluder 1510 comprises one or more discs that include a graft portion 1519 that is formed from foreign material. In one particular example, the occluder 1510 has a two disc configuration that includes a first disc 1513 and a second disc 1515, as shown in FIGS. 5E and 5F. The occluder 1510 additionally comprises a coupling or bridging component 1511 that links the first and second discs 1513, 1515. In some embodiments the bridging component 1511 may be formed integrally with the first and second discs 1513 and 1515, as shown. In other embodiments, the bridging component 1511 may be a separate component from the first and second discs 1513 and 1515. Each of the first and second discs 1513 and 1515 extend axially outwards from the bridging component 1511 and are configured for positioning on opposite sides of the septum 520 at the septal defect 518'. In some embodiments, each disc comprises a substantially thin or flat planar configuration. In other words, the occluder 1510 provides a configuration that allows the first and second discs 1513 and 1515 to straddle the septal defect 518', with a relatively planar surface of each disc for positioning against the septum 520. As such, the first and second discs 1513 and 1515 may provide sufficient contact with the septum 520 to ensure that the septal defect 518' is sealed by the occluder 1510. As mentioned above, the first and second discs 1513, 1515 are coupled together using a coupling or bridging component 1511. In some embodiments, the bridging component may be a tubular bridging component that extends between the two discs, as shown in FIGS. 5E and 5F. The height or thickness of the bridging component 1511 may vary as shown by the bridging components shown in FIGS. 5E and 5F. Furthermore, the occluder 1510 defines material first and second surfaces 1514 and 1516, formed by the outer surfaces of each of the first and second discs 1513, 1515. Additionally, the occluder 1510 comprises material third and fourth surfaces 1514' and 1516' formed by an inner surface of each of the first and second discs 1513 and 1515. These inner surfaces defined by material third and fourth surfaces 1514' and 1516' respectively are configured for resting against and substantially in contact with the surface of the septum 520 on either side of the septum 520. In some examples the occluder 1510 covers the aperture 518 defining the defect 518' and extends in a plane outside of the septum 520 with a portion of the occluder 1510 such as the bridging component 1511 extending within the aperture 518. In other embodiments the occluder 1510 may extend within the septum 520.

Figure 5H:
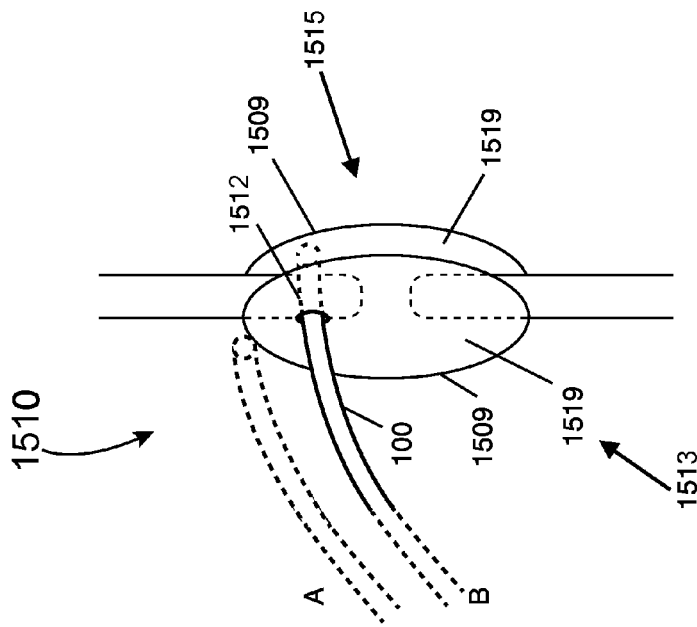
FIGS. 5G and 5H, are schematic views, illustrating one of more steps of a method for creating a channel in an occluder extending across an aperture formed in the heart of a patient in accordance with an embodiment of the present invention.
Figure 5G:
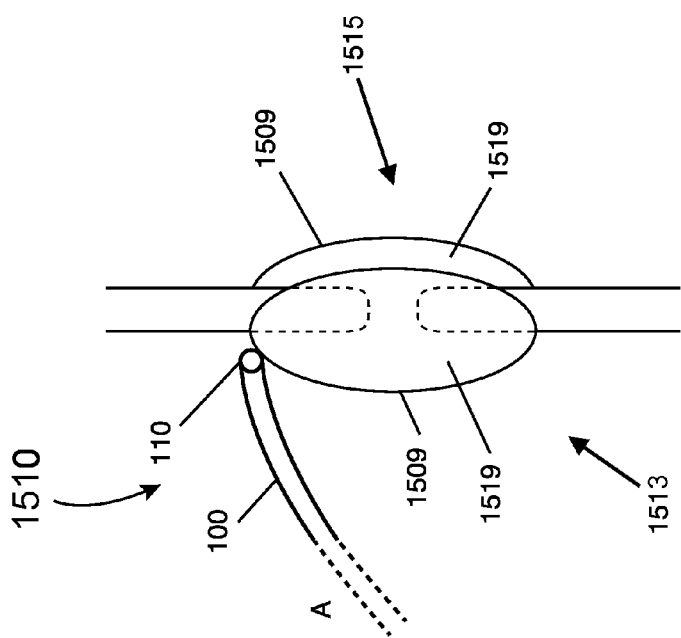

In some embodiments, as illustrated in FIGS. 5G and 5H, and as discussed previously, each of the first and second discs 1513 and 1515 comprise a graft portion 1519 which is formed from and comprises foreign material. In some embodiments, the foreign material forming the graft portion 1519 may be impermeable to fluids and thus functions to prevent the flow of blood when the occluder 1510 is placed across the septum 520. The occluder 1510 additionally includes a supporting structure or scaffold 1509 that is associated with the graft portion 1519 for supporting the graft portion 1519, as further illustrated in FIGS. 5G and 5H. For example the graft portion 1519 may be mounted on the supporting structure 1509 and maybe secured thereto. The supporting structure 1509 may comprise various configuration such a single wire frame or a mesh configuration among other configurations. In some embodiments the supporting structure 1509 comprises a metal scaffold. In other embodiments the supporting structure 1509 may comprise a polymer. In some embodiments, the first and second discs 1513 and 1515 may comprise one or more graft portions 1519.

In some embodiments, the graft portion 1519 (within each of the first and second discs 1513, 1515) may comprise one or more layers, which in some examples may be spaced apart from one another. In other words, the one or more layers may be separated from one another by a gap. In some embodiments, each of the one or more layers are individually mounted or secured onto the supporting structure 1509. In other embodiments, the one or more layers may be contiguous with one another forming a single unified layer. In some embodiments the foreign material forming the one or more layers of the graft portion 1519 may comprise a synthetic material. In some examples the synthetic material may be selected from the group consisting of polyethylene terephthalate (PET, for example Dacron®), cotton, a polyester material and fabrics thereof. In some specific examples, the polyester maybe a woven polyester fabric such as a monofilament twill woven fabric or a multi-filament tubular woven fabric. In still other embodiments, the polyester fabric may comprise extended polytetrafluoroethylene (ePTFE). Unexpectedly, radiofrequency energy delivered as described herein is able to create channels even through foreign material comprising stronger or more resilient material such as ePTFE or next-generation ePTFE.

In one specific example, the supporting structure or scaffold 1509 comprises a single wire frame or scaffold that is covered with a graft portion 1519. In a specific example of this, the single wire frame or scaffold is formed from a nickel-titanium alloy such as Nitinol and the graft portion 1519 comprises expanded poly-tetra-fluoro-ethylene (ePTFE). In other examples the supporting structure or scaffold 1509 comprises a mesh configuration, for example using a braided wire construction such as using braided Nitinol wires. The wire mesh may additionally have polyester fabric patches attached thereto which form the graft portion 1519. In some embodiments, the first and second discs 1513 and 1515 may have a uniform shape and depth/thickness. In other embodiments, the shape and/or thickness of each of the first and second discs 1513 and 1515 may vary. Additionally the size of each of first and second discs 1513 and 1515 may also vary. Alternatively, the discs 1513, 1515 may have a uniform size.

In some embodiments the first and second discs 1513, 1515 and may have a thickness or width w that is thinner than the width w' of the septum 520. In other embodiments, the widths w, w' may be comparable, as shown in FIGS. 5E and 5F. In still other embodiments, the width w of the first and the second discs may be thicker than the width w' of the septum 520.

A method in accordance with an embodiment of the present invention is now described with reference to FIG. 5D. Initially, the apparatus 100 is inserted through the inferior vena cava 502 into the right atrium 506 of the heart 500. In alternative embodiments, access to the right atrium 506 may be achieved via the superior vena cava 504 as described, for example, in U.S. patent application Ser. No. 11/265,304 (Filed on Nov. 3, 2005), now U.S. Pat. No. 7,947,040, which is incorporated herein by reference in its entirety. The apparatus 100 is then advanced towards the atrial septum 520 to position the electrode 110 adjacent the atrial septum 520. More specifically, as shown in FIG. 5D, the apparatus 100 is positioned within the right atrium 506 with the electrode 110 located substantially adjacent the material first surface 1514 of the first disc 1513 of the occluder 1510. Energy may then be delivered using the electrode 110. In a particular embodiment, radiofrequency energy may be delivered, for example, at about 5 W for a period of less than about 5 seconds. In other embodiments, energy may be delivered as described herein with respect to various embodiments outlined within the present application.

As the electrode 110 is energized with radiofrequency current a first channel portion 1512a is created within the foreign material forming the graft portion 1519 of the first disc 1513, as shown in further detail in FIG. 5E. More specifically, as energy is applied through the electrode 110 within the patient's body for example in the vicinity of tissue, a layer of water vapor may form around the electrode 110 which may facilitate generation of arcing at the electrode 110. The arcing may be sufficient to create the first channel portion 1512a through the foreign material. In some embodiments of the present invention, as energy is applied through the electrode 110, thermal energy is transferred from the electrode 110 to the foreign material. In some examples of this, the occluder 1510 may be encapsulated in tissue after having been implanted in the patient's body for a sufficient period of time. In other words, there may be endothelial cell growth over the graft portion 1519 of the occluder 1510, thus embedding/encapsulating the occluder 1510 in a layer of tissue. The tissue formed as such may function as a heat sink when energy is supplied through the electrode 110 and may retain thermal energy which is then transferred to the foreign material forming the graft portion 1519. In other words the tissue may function as a medium for transferring thermal energy from the electrode 110 into the foreign material of the graft portion 1519. As such, in some examples of the present invention delivering thermal energy may involve transfer of thermal energy into the foreign material via the tissue upon energizing the electrode 110 with the radiofrequency current. In some such instances the graft portion 1519 may comprise synthetic material.

Therefore, in accordance with some embodiments of the present invention, delivery of energy into the foreign material involves transfer of sufficient thermal energy to melt the foreign material to form a first channel portion 1512a through the graft portion 1519 of the first disc 1513. In some embodiments, this may be the primary mechanism for creating a channel within the foreign material. In other embodiments the mechanism of channel creation within the foreign material may primarily be due to arcing at the electrode 110. In further embodiments, channel creation results from a combination of thermal transfer as well as arcing. In some embodiments the electrode 110 may be positioned such that it is substantially adjacent the material first surface 1514. In some such embodiments the electrode 110 may be in contact with the material first surface 1514 to allow the electrode 110 to substantially melt the foreign material upon energizing the electrode 110 with radiofrequency current to create the first channel portion 1512a through the first disc 1513. In embodiments where the graft portion 1519 comprises one or more layers of foreign material, the first channel portion 1512a extends through the one or more layers.

In some embodiments, the energy may be delivered substantially continuously as apparatus 100 is advanced through the occluder 1510. The first channel portion 1512a forms a portion of channel 1512 that is formed through the occluder 1510. First channel portion 1512a is formed through the graft portion 1519 and extends between the inner and outer surfaces of the first disc 1513 defined by the material first and third surfaces 1514 and 1514'. As such the delivery of energy through the electrode 110 forms a channel 1512 at least partially between said material first and second surfaces 1514 and 1516 of the occluder 1510. In some embodiments the first channel portion 1512a extends substantially continuously between the material first and third surfaces 1514 and 1514'. In other embodiments the first channel portion 1512a created by electrode 110 may extend between the material first and third surfaces 1514 and 1514' at spaced apart intervals that may be separated by a gap for instance (for example in instances where the graft portion 1519 comprises one or more layers).

The apparatus 100 may then be advanced further, substantially while energy is being delivered to create a channel 1512b' through the septum 520. In some instances as energy is delivered through the electrode 110 a layer of water vapor forms around the electrode 110 and arcing is generated allowing the electrode 110 to perforate the tissue at the septum 520, thus creating channel 1512*b*' through the tissue. The apparatus 100 may be continued to be advanced while still delivering energy through the electrode 110 until the electrode 110 is positioned at the second disc 1515 adjacent the material fourth surface 1516' of the occluder 1510. As energy continues to be delivered, a second channel portion 1512*c* is created through the foreign material forming the graft portion 1519 of the second disc 1515, allowing the apparatus 100 to traverse the occluder 1510 and exit the material second surface 1516. The first and second channel portions 1512*a* and 1512*c* may be substantially aligned along the path of the apparatus 100. As such the one or more channel portions created using the apparatus 100 may be aligned along the trajectory of the apparatus 100.

Figure 5I:
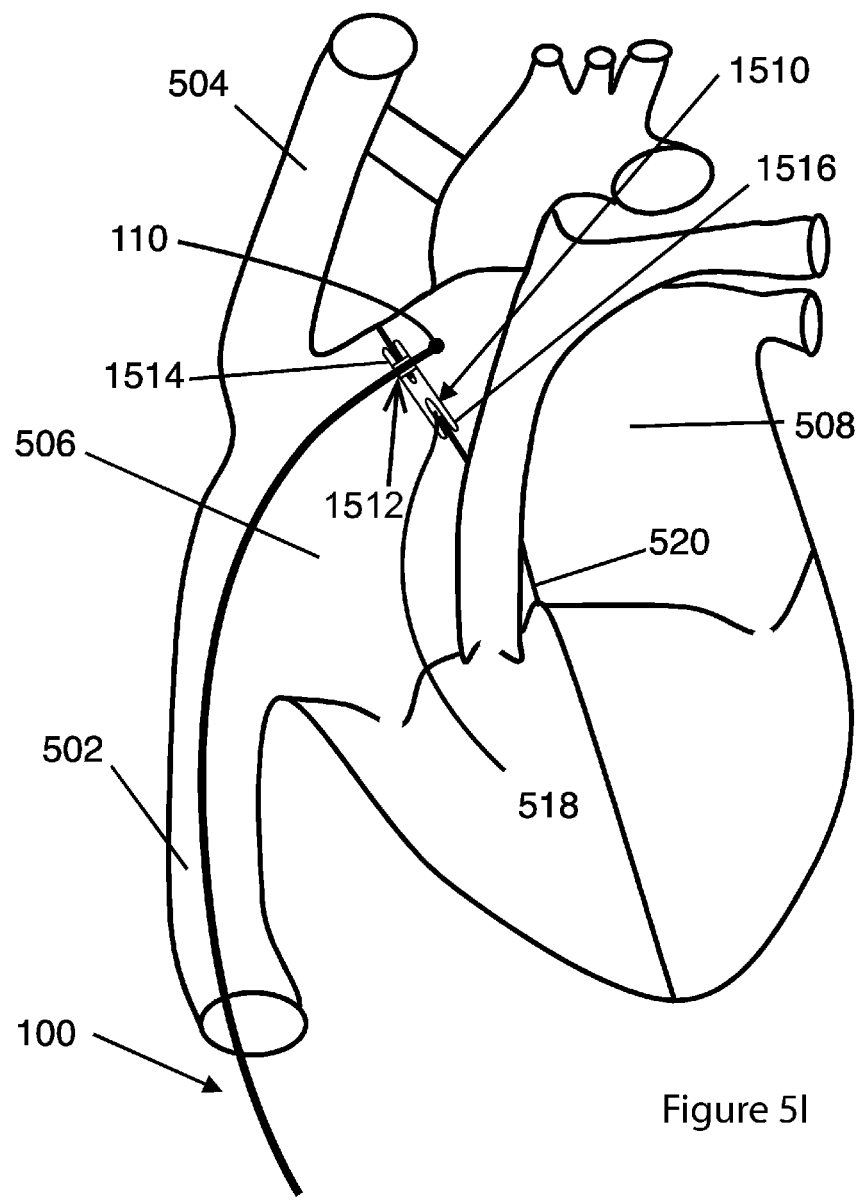
FIG. 5I, in a schematic view, illustrates one of more steps of a method for creating a channel in an occluder extending across an aperture formed in the heart of a patient in accordance with an embodiment of the present invention.

FIG. 5I shows the apparatus 100 positioned in the left atrium 508 after being advanced through the channel portion 1512*c* that is formed within the second disc 1515 of the occluder 1510. The mechanism of advancement and channel formation through the second disc 1515 may be substantially similar to the mechanism of advancement through the first disc 1513. As outlined in FIG. 5E, the second channel portion 1512*c* extends between inner and outer surfaces of the second disc 1515 defined by material fourth and second surfaces 1516' and 1516, respectively. As such a channel 1512 is formed through the occluder 1510 that includes one or more channel portions such as first and second channel portions 1512*a* and 1512*c* through the occluder 1510, as well as channel 1512*b*' through the tissue of the septum 520. The channel 1512 thus formed extends at least partially between material first and second surfaces 1514 and 1516 of the occluder 1510. Creation of the channel 1512 provides access into the left atrium 508 to enable additional medical instruments to be advanced there-through for treating the left side of the heart 500. Each of the channel portions 1512*a*, 1512*c* and channel 1512*b*' may be dilated using one or more of a dilator and a balloon and a secondary medical device such as a delivery catheter or an ablation catheter that may be advanced across the channel 1512 to be placed within one of the left chambers of the heart to treat an area therein.

In some embodiments, energy delivery may be substantially continuous as the apparatus 100 is advanced. In alternate embodiments, energy delivery may not be substantially continuous and may be delivered intermittently. For example, once the apparatus 100 has created respective channel portions through the foreign material within each of the first disc 1513, septum 520 and the second disc 1515, energy delivery may be stopped. In other words, energy delivery is stopped after each channel portion is created within the occluder 1510. For example energy delivery is stopped after each of the channel portions 1512*a* and 1512*c* are created. Additionally energy delivery may also be stopped after channel 1512*b*' is created within the septum 520. In embodiments where the graft portion 1519 included within each of the discs comprises one or more layers, energy delivery may be stopped after formation of a channel portion within each of the one or more layers.

In alternate embodiments, the graft portion 1519 of the occluder 1510 comprises one or more layers that include foreign material. In some examples these layers may be spaced apart from one another. In a further example, these independent layers may be moveable relative to one another. Thus, a gap may exist between the multiple layers. In some specific embodiments, the graft portion 1519 may comprise two layers. In other embodiments the graft portion 1519 may comprise more than two layers.

In some embodiments, the foreign material forming the one or more layers of the graft portion 1519 may comprise a synthetic material. In one such embodiment, each of the first and second disc 1513 and 1515 comprise a graft portion 1519 that comprises more than one layer and the graft portion 1519 is supported by a scaffold 1509 that is formed by a single wire frame. In accordance with such an embodiment a first channel portion 1512*a* is created that extends through the one or more layers of the first graft portion 1519 of first disc 1513. In some embodiments, the mechanism of channel formation, for example via arcing as described hereinabove, may be assisted by water vapor formation between the multiple layers of the graft portion 1519. The multiple layers may function to trap a vapor bubble there-between thereby facilitating arcing for creation of a first channel portion 1512*a* through the multiple layers. In a specific example, the mechanism of advancement though septum 520 may be similar to the mechanism described previously. Once the apparatus 100 crosses the septum 520, a second channel portion 1512*c* is created through the multiple layers within the graft portion 1519 forming the second disc 1515 in a similar fashion to the first channel portion 1512*a*. As an additional advantage, the one or more layers may facilitate channel creation as they may allow the apparatus 100 to tent/displace the foreign material forming the independent layers more easily and as such may facilitate advancement of the apparatus through the graft portion 1519.

In an alternative embodiment as shown in FIG. 5F, the occluder 1510 may comprise a bridging component 1511 that is substantially wider than the outer diameter of the apparatus 100, allowing the apparatus 100 to create a channel 1512 along the bridging component 1511. Similar to embodiments described herein above, apparatus 100 may be positioned against material first surface 1514 of the occluder 1510. Energy may then be applied through electrode 110 as the apparatus 100 is advanced through the first disc 1513 creating a first channel portion 1512*a* through the foreign material forming the graft portion 1519. In some embodiments as shown in FIG. 5F, the inner surfaces of the first and second discs 1513, 1515, as defined by material third and fourth surfaces 1514',1516' are positioned adjacent and in abutting contact with the bridging component 1511 and as such are embedded within the occluder 1510. Thus, as the apparatus 100 is advanced, it passes through the material third surface 1514' and into the bridging component 1511 creating an intermediate channel portion 1512*b* there-through. The apparatus 100 as it is advanced then passes through material fourth surface 1516' and is thereafter advanced across the foreign material forming the graft portion 1519 of the second disc 1515. The apparatus subsequently exits through the material second surface 1516 of the second disc 1515 to create a second channel portion 1515*c* there-through. As such, a channel 1512 is formed through the occluder 1510 and it comprises channel portions 1512*a*, 1512*b* and 1512*c*. Thus, the channel 1512 extends between material first and second surfaces 1514 and 1516. The channel portions 1512*a*, 1512*b* and 1512*c* may be aligned along the path of the apparatus 100 through the occluder 1510. In alternate embodiments, the channel 1512 may comprise a channel portion formed in only one of the first and second discs 1513, 1515 positioned on either side of the septum 1520. For example if the path of the apparatus 100 is at an angle that allows it to pass through only one disc or if the size of one of the first and second discs 1513, 1515 is substantially smaller than the other.

In some embodiments, as mentioned previously, the occluder 1510 (and as such, the foreign material forming the graft portion 1519) may be embedded in tissue after having been implanted within a patient's body for a period of time, as there may be tissue growth over the occluder 1510. This may facilitate creation of a layer of water vapor to facilitate arcing as energy is applied through the electrode. Furthermore, the tissue may function as a heat sink and may function to transfer heat to the foreign material forming the graft portion 1519 of the occluder to facilitate channel creation. In some such embodiments a method of channel creation may provide for waiting for a period of time after implanting an occluder 1510 within the patient's body prior to attempting to create a channel 1512 through the occluder. In some embodiments, a method of channel creation may provide for waiting for at least a year prior to attempting to create a channel 1510 through the occluder 1510. In some embodiments, the method may additionally provide for cauterizing loose threads of the fabric or material forming the graft portion 1519 as RF energy is applied to create a channel portion. In some instances this may help prevent or minimize tearing of the graft portion 1519.

Thus, in one particular application, some embodiments of the present invention provide a method for creating a channel 1512 through a foreign material located in a body of a patient using radiofrequency energy, where the foreign material is included within a graft portion 1519 that extends across the septum 520 for repairing a septal defect 518'. The foreign material defines a material first surface 1514 and a substantially opposed material second surface 1516. The method provides for creating the channel 1512 that extends through the foreign material at least partially between the material first and second surfaces 1514 and 1516. The method uses an apparatus 100 including the electrode 110 where the method comprises positioning the electrode substantially adjacent to the material first surface 1514 and involves energizing electrode 110 with a radiofrequency current to deliver energy into the foreign material to create the channel 1512.

Additionally as outlined above, some embodiments of the present invention provide a method for gaining access into a left side of a heart 500, in cases where foreign material extends across the septum 520 of the heart, for example within an occluder 1510 that extends across the septum 520 for repairing a septal defect 518'. These embodiments of the present invention provide a method of gaining access into a left side of a heart 500, using an apparatus 100 that includes an electrode. The method involves positioning the electrode 110 substantially adjacent to the foreign material within the occluder 1510, and delivering energy into said foreign material by energizing the electrode 110 with radiofrequency current to create a channel 1512 within the foreign material within the occluder 1510 to allow the apparatus 100 to cross the septum 520 through the channel 1512 to gain access into the left side of the heart.

Application 2-Peripheral Vascular Procedures

In a further application, an embodiment of a method according to the present invention may be useful, for example, to create a channel within a graft composed of foreign material. In some embodiments, the graft is associated with a substantially tubular supporting structure, for example a stent, located within an elongated vessel of the body of the patient. In some such embodiments, the method is performed in order to restore blood flow to a branch of the elongated vessel being occluded by the graft material, thus substantially preventing fluid communication between the branch and the elongated vessel, by creating a channel through the material.

Example 2A

With reference now to FIGS. 6A, 6B, 7A and 7B, methods for in-situ creation of a channel through a stent-graft are illustrated. In the illustrated embodiments, a stent-graft 606, composed of a foreign material, has been placed to cover an aneurysm 604 in an abdominal aorta 600. As shown in these figures, stent-graft 606 occludes the renal arteries ostia 605.

This positioning of the stent-graft 606 is typically necessitated by an inadequate, i.e. too short, proximal neck of the abdominal aorta 600. One of the greatest challenges of stent-grafting an abdominal aortic aneurysms 604 is to obtain a long proximal attachment site to ensure a good seal without occluding the renal or supra-aortic vessels. If a long proximal site is unavailable, the ostia of the renal and/or supra-aortic vessels may become occluded by the stent-graft 606. The present invention provides a method for creating a transluminal in-situ channel in order to restore blood flow to any vessels that do become occluded during the course of such a procedure.

Figure 6A:
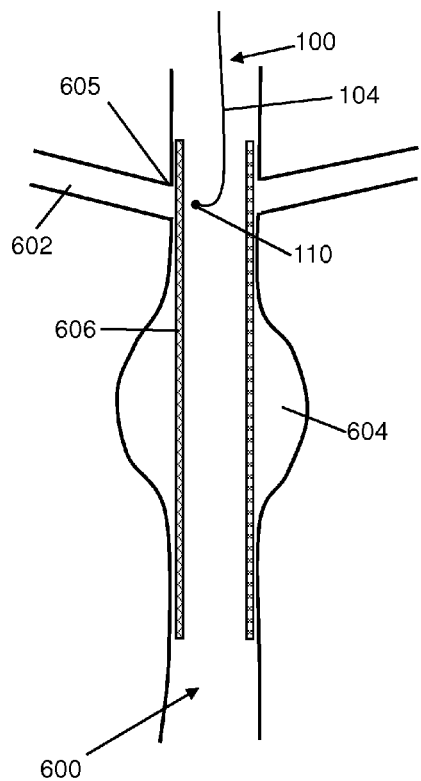
FIGS. 6A and 6B, in schematic views, illustrate a method for creating a channel in a stent graft extending across an ostium of a renal artery of a patient in accordance with an embodiment of the present invention.
Figure 6B:
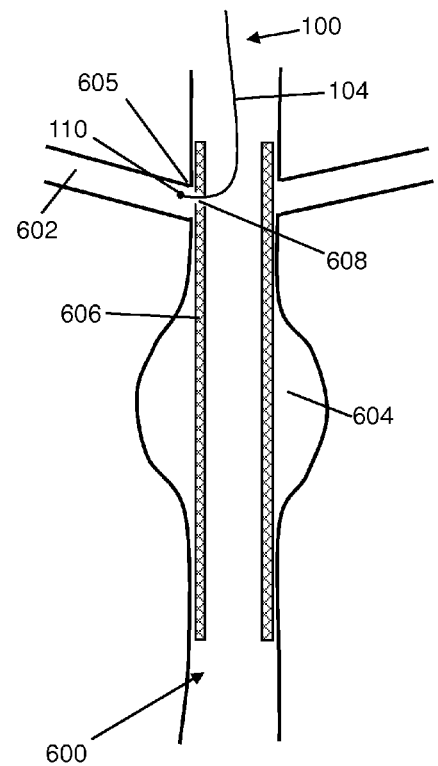

With reference first to FIGS. 6A and 6B, an antegrade approach to in-situ channel creation is provided. In this approach, the distal end region 104 is introduced into the body of the patient through the body vasculature inside the thoracic cavity, or in other words from a position superior to the diaphragm of the patient, and advanced towards the abdominal aorta 600 in which the electrode 110 is then positioned. FIG. 6A shows the electrode 110 of the apparatus 100 positioned in the abdominal aorta 600 substantially opposite the renal artery ostium 605, which is occluded by the stent-graft 606. At this point, energy may be delivered from an energy source through the electrode 110 in order to create a channel 608, as seen in FIG. 6B, in or through the stent-graft 606. FIG. 6B shows the electrode 110 after it has been advanced through the channel 608 into the renal artery 602. Creation of the channel allows for fluid communication and restoration of blood flow between the abdominal aorta 600 and the renal artery 602. At this point, as described above with respect to FIG. 4, the channel 608 may be dilated using one or more of a dilator and a balloon (for example a cutting balloon) and a stent may be placed across the channel 608 to maintain the patency of the renal artery 602.

Figure 7A:
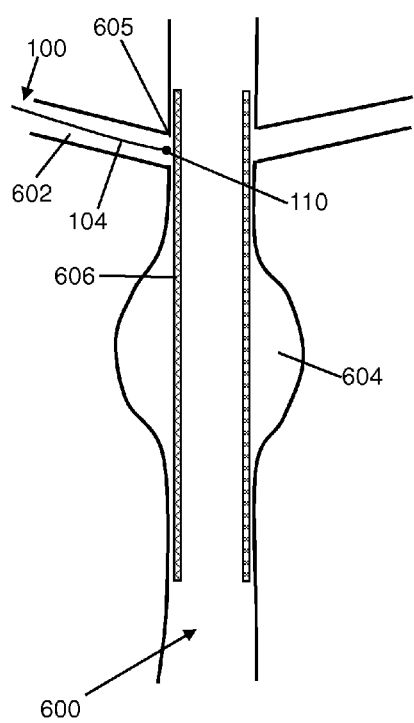
FIGS. 7A and 7B, in schematic views, illustrate a method for creating a channel in a stent graft extending across an ostium of a renal artery of a patient in accordance with an alternative embodiment of the present invention.
Figure 7B:
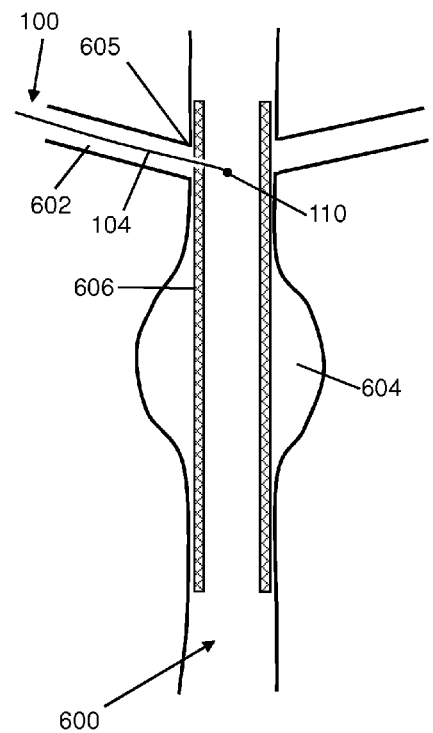

With reference now to FIGS. 7A and 7B, a retrograde approach is illustrated. In this approach, introducing the distal end region 104 into the body of the patient includes introducing the distal end region into the body vasculature and through the renal artery 602 towards the abdominal aorta 600. In such an embodiment, positioning the electrode 110 substantially adjacent to a material first surface then includes positioning the electrode 110 substantially adjacent to the renal artery ostium 605 outside of the abdominal aorta 600.

With reference first to FIG. 7A, the electrode 110 of the apparatus 100 is positioned in the renal artery 602 at the renal artery ostium 605, which is occluded by the stent-graft 606. At this point, energy may be delivered from an energy source through the electrode 110 in order to create a channel 608 in or through the stent-graft 606. FIG. 7B shows the electrode 110 after it has been advanced through the channel 608 into the abdominal aorta 600. As mentioned hereinabove, creation of the channel 608 may allow for fluid communication and the restoration of blood flow between the abdominal aorta 600 and the renal artery 602. At this point, as described above with respect to FIG. 4, the channel 608 may be dilated using one or more of a dilator and a balloon (for example a cutting balloon) and a stent may be placed across the channel to maintain the potency of the renal artery. It should be noted that in the embodiment of FIGS. 7A and 7B, step 404 of the method comprises obtaining access to renal artery 602, for example during a surgical procedure or via a deep puncture.

It should be noted that, although this example has been described in conjunction with treatment of an abdominal aortic aneurysm, a similar method is also contemplated for treating a thoracic aortic aneurysm, whereby a subclavian artery, for example, may become occluded by a stent-graft. Such a condition may be more easily treated using a retrograde approach, by inserting an apparatus through the subclavian artery towards the aorta. In addition, vessels other than the renal arteries 602 may be occluded by an abdominal aortic stent-graft, for example the mesenteric arteries (not shown in the drawings). Alternatively, similar embodiments of the method may be practiced in other situations whereby a vessel ostium (or any portion of an elongated vessel, tube and/or duct) in a patient's body is occluded by a foreign material.

Example 2B

With reference now to FIGS. 8A-8D, alternate methods for in-situ creation of a channel through a stent-graft are illustrated. In the illustrated embodiments, a stent-graft 806, composed of a foreign material, has been placed to cover an aneurysm 804 in a section of the descending aorta, more specifically, within the thoracic aorta 800. As shown in these figures, the stent-graft 806 occludes the opening or ostium 805 of the Left Subclavian Artery (LSA) 802.

In the illustrated example, the positioning of the stent-graft 806 at the LSA ostium 805 is necessitated by the proximity of the LSA ostium 805 to the site of the aneurysm 804. A challenge is generally presented when an aneurysm 804 occurs within a vessel near an ostium of a side branch vessel, such as the LSA 802. It may become difficult to place the stent-graft 806 within the vessel to ensure protection of the aneurysm 804 while maintaining patency of the side branch ostium. In one such example, the aneurysm 804 and the LSA ostium 805 are located substantially adjacent each other. "Adjacent" may be taken to mean next to, in proximity to, near to, or in the vicinity of. In one example the aneurysm 804 and the LSA ostium 805 are located opposite to one another along the coronal and/or saggital planes. In other words, the aneurysm 804 and the LSA ostium 805 are radially opposed to one another. In a further example, the aneurysm 804 and the ostium 805 may be positioned axially adjacent to one another. In other words, the aneurysm 804 and the LSA ostium 805 may be positioned substantially collinearly with respect to each other. Thus, the proximity of the aneurysm 804 to the LSA ostium may necessitate the positioning of the stent-graft 806 such that it covers the aneurysm 804 but also occludes the LSA ostium. This positioning of the stent-graft 806 is typically necessitated by an inadequate, i.e. too short, proximal neck of the thoracic aorta 800. One of the greatest challenges of stent-grafting a thoracic aortic aneruysm 804 is to obtain a long proximal attachment site to ensure a good seal without occluding any of the side branch vessels such as the Left Subclavian Artery (LSA) 802, the Right Subclavian Artery (RSA) 808', Left Common Carotid Artery (LCCA) 810 or Right Common Carotid Artery (RCCA) 812. If a long proximal site is unavailable, then an ostium of a side branch vessel may become occluded by the stent-graft 806. For the specific case shown in FIGS. 8A-8D, to treat a thoracic aortic aneurysm, the LSA ostium may become occluded by the stent-graft 806. This illustrated embodiment of the present invention provides a method for creating a transluminal in-situ channel in order to restore blood flow to any vessels that do become occluded during the course of such a procedure.

Figure 8A:
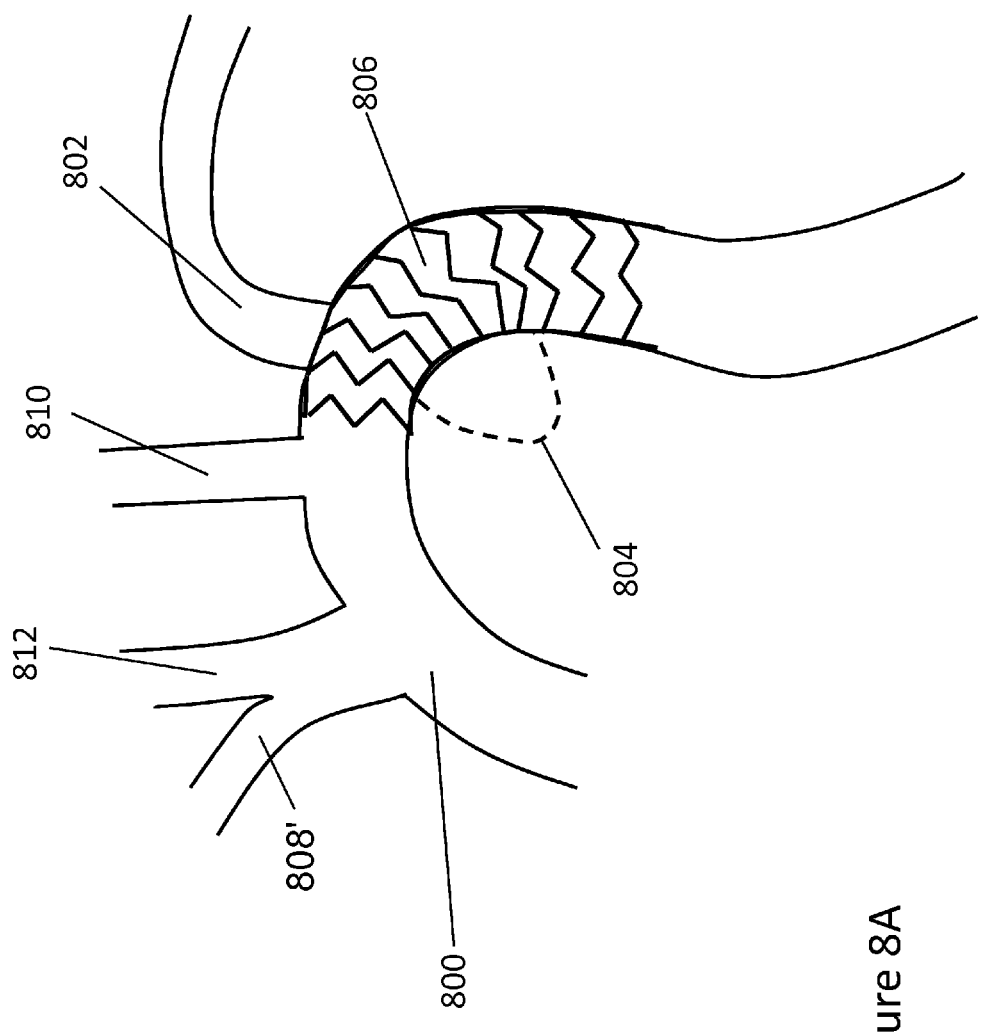
FIGS. 8A and 8B, in schematic views illustrate a method for creating a channel in a stent graft extending across an ostium of a left Subclavian Artery (LSA) of a patient in accordance with an alternative embodiment of the present invention.
Figure 8C:
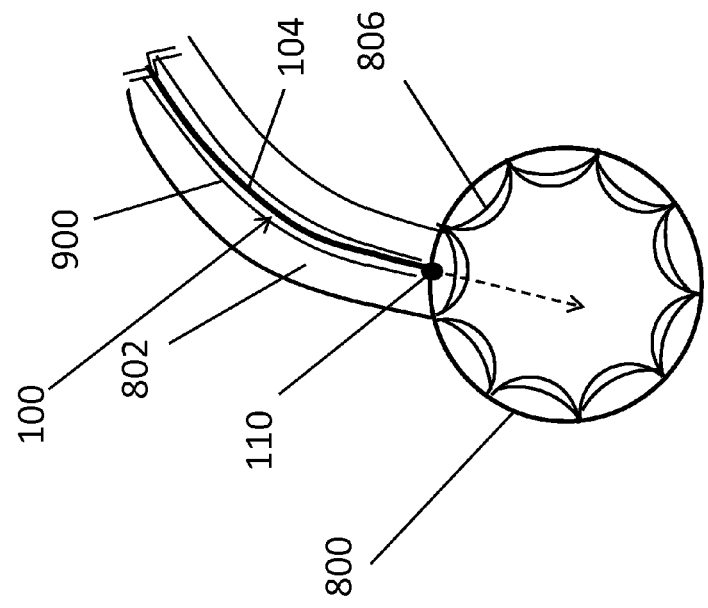
FIG. 8C is a right anterior oblique view illustrating a method for creating a channel in a stent graft extending across an ostium of a left Subclavian Artery (LSA) of a patient in accordance with an alternative embodiment of the present invention.
Figure 8B:
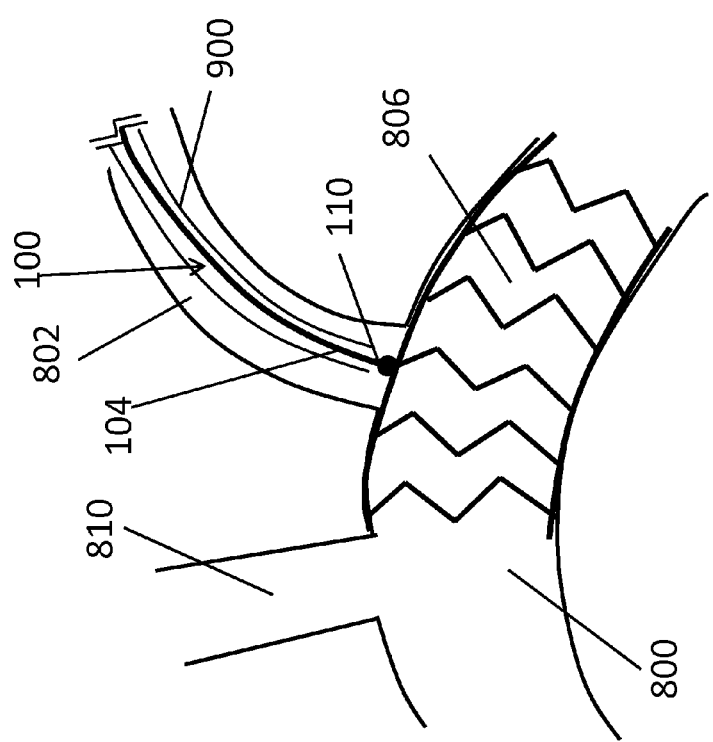

With reference first to FIGS. 8B, and 8C, a retrograde approach to in-situ channel creation is illustrated. In this approach, introducing the distal end region 104 of apparatus 100 into the body of the patient includes introducing the distal end region 104 into the body vasculature and through the left subclavian artery (LSA) 802 towards the thoracic aorta 800. In one specific example, a guide sheath 900 is introduced into the body of the patient through the body vasculature and advanced into the LSA via the left brachial artery. The sheath 900 is advanced till a distal end of the sheath 900 is located about 5 cm from the stent-graft 806. The apparatus 100 according to an embodiment of the present invention, along with a guide catheter (not shown), is then be inserted through the guide sheath 900. The distal end region 104 of apparatus 100 is then advanced towards the LSA such that the electrode 110 is positioned adjacent the stent-graft 806 that is occluding the LSA ostium 805. In such an embodiment, positioning the electrode 110 substantially adjacent to a material first surface includes positioning the electrode 110 substantially adjacent to the LSA ostium 805 outside of the thoracic aorta 800. In some embodiments, a curved guide catheter or a centering mechanism may be used to direct the apparatus 100 towards the center of the LSA to position electrode 110 at the desired target location. In one example, a balloon catheter may be used to centre the apparatus 100 within the vessel.

When creating a channel through a stent-graft such as stent-graft 806, a strut 807 of the stent forming the stent-graft 806 may obstruct advancement of apparatus 100 through the stent-graft 806. In some embodiments of the present invention, a guide catheter is used to direct the apparatus 100 around the strut 807, as follows: The guide catheter and apparatus 100 may be aligned with the stent such that they are positioned against the strut 807. Gentle buckling of the catheter/apparatus assembly may be used to confirm that the catheter/apparatus assembly is positioned against the stent. The guide catheter may be incrementally adjusted around the strut 807 such that it is no-longer blocked by the strut 807. In some embodiments, a Right Anterior Oblique (RAO) view under fluoroscopic imaging may be used to guide the catheter and the apparatus 100 to the appropriate position.

Once the electrode is positioned appropriately, energy is delivered through the electrode 110 to puncture through the graft to create a channel 808 there-through. In some embodiments, the energy may be applied at a voltage of about 400 Vrms, with a duty cycle of 25 ms ON/975 ms OFF. In one particular example, energy is applied using the Baylis RFP-100A Generator at a high power setting for 2 seconds to puncture the graft/fabric of the stent-graft. In another example, it may be sufficient to deliver energy twice at durations of 1 second. The apparatus 100 may then be advanced into the stent-graft 806 under fluoroscopic guidance. In some embodiments, the energy may be delivered with the power being in the range of between about 30 Watts to about a 100 Watts; and the voltage may be in the range of between about 300 Vrms to about 500 Vrms. In some embodiments the energy may be applied for duration of at least 25 ms. Furthermore, in some embodiment the ON period of the duty cycle may range from between about 25 ms to about 1000 ms.

Figure 8D:
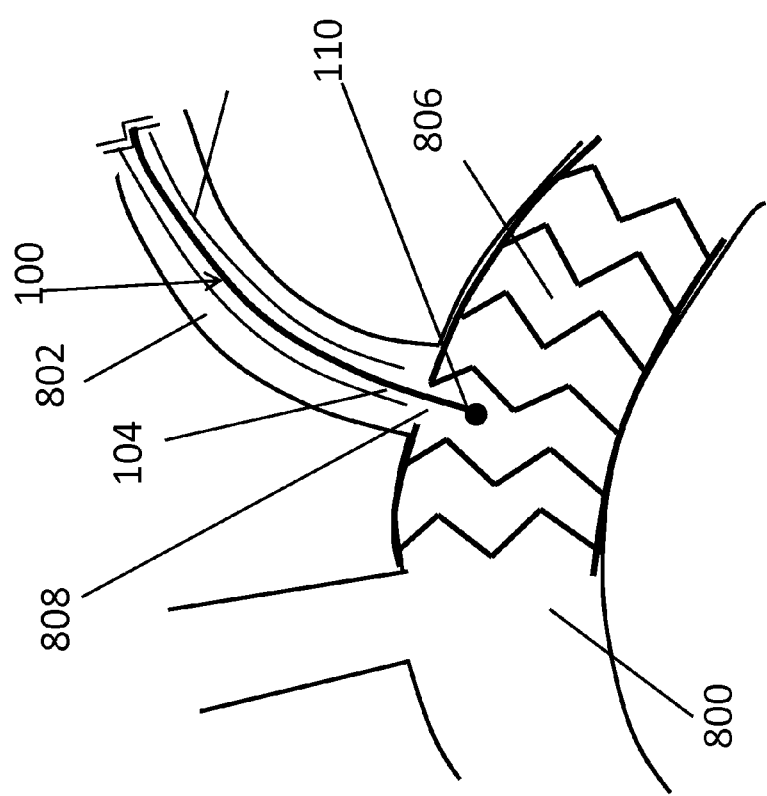
FIG. 8D, in schematic view illustrates a method for creating a channel in a stent graft extending across an ostium of a left Subclavian Artery (LSA) of a patient in accordance with an alternative embodiment of the present invention.

FIG. 8D shows the electrode 110 after it has been advanced through the channel 808 into the thoracic aorta 800. As mentioned hereinabove, creation of the channel 808 may allow for fluid communication and the restoration of blood flow between the thoracic aorta 800 and the LSA 802. At this point, as described above with respect to FIG. 4, the channel 808 may be dilated using one or more of a dilator and a balloon (for example a cutting balloon) and a stent may be placed across the channel to maintain the patency of the LSA. It should be noted that in the embodiment of FIGS. 8B and 8C, step 404 of the method comprises obtaining access to LSA 802, for example during a surgical procedure or via a deep puncture.

With reference now to FIGS. 9A and 9B, an antegrade approach to in-situ channel creation is provided. In this approach, the distal end region 104 is introduced into the body of the patient through the body vasculature and advanced towards the thoracic aorta 800 in which the electrode 110 is then positioned. In one specific example, femoral access is used to guide the distal end region 104 of the apparatus 100 into the lumen of the stent-graft 806 that is positioned within the thoracic aorta. FIG. 9A shows the electrode 110 of the apparatus 100 positioned in the thoracic aorta 800 substantially opposite the left subclavian artery (LSA) ostium 805, which is occluded by the stent-graft 806. At this point, energy may be delivered from an energy source through the electrode 110 in order to create a channel 808, as seen in FIG. 9B, in or through the stent-graft 806. FIG. 9B shows the electrode 110 after it has been advanced through the channel 808 into the left subclavian artery (LSA) 802. Creation of the channel allows for fluid communication and restoration of blood flow between the thoracic aorta 800 and the LSA 802. At this point, as described above with respect to FIG. 4, the channel 808 may be dilated using one or more of a dilator and a balloon (for example a cutting balloon) and a stent may be placed across the channel 808 to maintain the patency of the LSA 802.

A method for transluminal in-situ channel formation, for example as described herein, allows for more accurate placement of the channel, less reliance on preoperative imaging, increased availability and decreased cost of a "universal", non-customized graft, and eventually, more accessibility for a greater number of patients to the advantages of endovascular repair. As well, the technique could be used as a 'salvage' procedure when inadvertent coverage of side branches occurs. Most importantly, it would allow more accurate placement of the channels with the stent-graft in place in the aorta, rather than based on preoperative radiographic imaging.

General Features

An additional challenge that may be faced when creating a channel through a septal occluder or stent-graft using radiofrequency energy is contact of the energized electrode with a (electrically conductive) metallic structure, for example scaffold 1509 of occluder 1510 or strut 807 of stent-graft 806. Embodiments of the present invention provide a method for indicating a metal contact error if the electrode 110 of the apparatus 100 is in contact with the metallic structure. In accordance with such embodiments, the energy delivery system prevents delivery of energy when the electrode 110 is positioned adjacent to or in contact with the metallic structure but allows the apparatus 100 to delivery energy near the metallic structure. This allows the physician to continue to deliver energy from the electrode 110 and steer the electrode 110 away from the metallic structure.

Thus, the orientation or position of the electrode 110 may be re-adjusted by moving it around or away from the metallic structure, while power is being delivered, which thereby allows the user to deliver energy from electrode 110 while it is positioned close to the metallic structure to cut through the stent-graft 806 or graft portion 1519, but generating a "metal detect" error if the electrode 110 is in contact with the metallic structure or close enough to produce undesired arcing.

In some embodiments the method of the present invention may additionally provide a means for determining if the apparatus 100 has been positioned against a metallic component or structure and thus may allow repositioning of the device to allow it to be positioned against the foreign material to allow a channel to be created there-through.

FIG. 10 is a flow chart illustrating an example of such a method. As shown by step 1004, an energy delivery device such as apparatus 100 may be positioned within a region of tissue at a target location within a patient's body. At step 1006, an RF power source may be used to supply RF energy to the apparatus 100. An energy delivery parameter, for example the current output from the ground return pathway of the apparatus 100, is monitored. The measured values of the current are compared to a predetermined current range or magnitude threshold.

At step 1008, the measured current is analyzed to determine if it is greater than the predetermined threshold or range. If the current has peak currents that exceed the current magnitude threshold or normal operational currents, at step 1010 an excess current or over-current is recorded. If the monitored current is within the range of normal operational currents (below the predetermined current threshold), then the delivery of energy through the energy delivery device will not be interrupted and energy delivery can continue at step 906 and the current can continue to be monitored. At step 1012, a determination is made to assess whether or not the extent of over-currents recorded within a time period is greater than a predetermined sensitivity threshold and, if it is, then the energy delivery may be adjusted at step 1014. In one example, adjustment of the energy delivery comprises stopping the delivery of energy. In some embodiments, the extent of over-currents recorded may be determined in terms of the sum or magnitude of the over-currents recorded. In other embodiments, the extent of over-currents recorded may be determined in terms of the number or quantity of over-currents recorded. If the extent of over-currents is below the sensitivity threshold, then at step 1006 the energy delivery is continued while monitoring the current to allow the apparatus 100 to create a channel through the foreign material.

Further details regarding the generation of a "metal detect" error as described hereinabove are found in U.S. provisional application No. 61/448,578 previously incorporated herein by reference in its entirety as well as in U.S. patent application Ser. No. 13/410,868, filed on Mar. 2, 2012, also incorporated herein by reference in its entirety.

Specific examples of this feature are described herewith for use in both peripheral as well as cardiac procedures.

Example 3A

Metal Detect for Facilitating Cardiac Septal Procedures

In some embodiments the method of the present invention may additionally provide a metal detect feature for facilitating channel creation within an occluder 1510 positioned within a septum 520 of the heart 500 to facilitate the method of channel creation outlined previously with respect to FIGS. 5A-5I. The method provides a means for detecting or determining/assessing if the electrode 110 of apparatus 100 is positioned adjacent a metallic support structure such as the metal scaffold 1509 of an occluder 1510. If it is determined that the apparatus is in contact with the metal scaffold 1509, then energy delivery may be controlled and/or the path of the apparatus 100 may be altered. Thus, the method may allow repositioning of the device to allow it to be positioned against the foreign material forming the graft portion 1519 of the occluder 1510 to facilitate creation of a channel 1512 through the occluder 1510.

A specific example of a method of the present invention is illustrated in FIGS. 5G and 5H. With reference to now to FIG. 5G, once the apparatus 100 is positioned within the heart, the apparatus 100 may be advanced to be positioned adjacent the occluder 1510. The metal detect feature is discussed further herein with reference to FIG. 10.

In some embodiments, the step of detecting or determining whether the electrode 110 is positioned adjacent the metal scaffold 1509 may involve using a technique that detects a parameter of energy delivery at the output of the electrode 110. In some embodiments, the parameter of energy delivery comprises output impedance or output current. As such, the technique may involve measuring impedance or current at the output of the electrode 110, and these measured values may be compared to known predetermined values to determine if the measured values are indicative of contact with metal scaffold 1509 (or indicative of the fact that the electrode is in the vicinity of the metal scaffold 1509). For example, a lower impedance (or a decrease in impedance) may indicate that the electrode is positioned substantially adjacent the metal scaffold 1509. Alternatively, a higher current value at the output (or an increase in output current) may indicate that the electrode is positioned substantially adjacent the metal scaffold 1509. In some embodiments, over-currents at the output may be detected and the extent of this over-current may be determined in order to determine if the apparatus 100 is in contact with the metal scaffold 1509.

Alternatively, determining that the electrode 110 is adjacent a metal scaffold 1509 may involve measuring or otherwise obtaining tactile feedback, and/or a means of visualization using imaging techniques. In some embodiments of the present invention, the step of detecting whether or not the electrode 110 is positioned adjacent the metal scaffold 1509 is performed substantially automatically, for example by a component of the generator.

In the example shown, the metal scaffold 1509 of the occluder 1510 is formed from a single wire frame that wraps around the periphery of the occluder 1510. Path A in FIG. 5H illustrates one example of a path that may be taken by the apparatus 100 when it is positioned within the right atrium of the heart 500. In the example shown, the apparatus 100 is positioned against the single wire metallic frame forming the scaffold 1509 at the periphery of the occluder 1510. Once it is detected that the apparatus 100 is adjacent or in contact with the metallic frame, the apparatus 100 is re-positioned along path B by guiding the apparatus 100 away from the periphery of the occluder 1510, so that it is positioned adjacent the foreign material within the graft portion 1519 of the occluder 1510. This allows the apparatus 100 to cross the occluder 1510 by creating a channel portion 1512a through the first disc by delivering energy through the electrode 110 as discussed previously with reference to FIGS. 5A-5I. A channel portion 1512b may similarly be created through the disc 1515 to cross the occluder 1510.

In some embodiments, once a metal scaffold 1509 is detected in the path of the apparatus 100, the method may additionally involve stopping the delivery of energy prior to guiding the apparatus away from the metal scaffold 1509. The electrode 110 may then be re-energized once the apparatus 100 is guided away from the metal scaffold 1509 to be positioned adjacent the foreign material. In some embodiments where the metal scaffold 1509 of the occluder 1510 comprises a mesh configuration, the method as described herein may allow the apparatus 100 to be advanced through the openings within the mesh configuration. In other words, the method and, specifically, the 'metal detect' feature described herein may allow the apparatus 100 to be advanced through holes or gaps already present in the existing mesh configuration (i.e. gaps between the metallic portions) while avoiding contact with the struts that form the mesh configuration. This facilitates channel creation through the graft portion(s) while providing a means to avoid delivery of energy into the metallic mesh configuration which may reduce risk of injury to the patient and may additionally reduce the risk of damage to the structural integrity of the metal scaffold 1509 due to thermal damage.

Example 3B

Metal Detect for Facilitating Peripheral Interventional Procedures

Such a method as described above can be utilized to prevent delivery of energy to the electrode 110 when it would be detrimental to the patient to do so, for example when the electrode is positioned too close to a strut of the stent graft. Thus, in one specific example, the metal detect feature and method outlined above can be used to facilitate peripheral vascular interventional procedures, for example, where a stent-graft has been positioned within body vasculature. More specifically, the metal detect feature can be utilized in procedures outlined previously with reference to FIGS. 6A-9B to assist in the creation of a channel through a stent-graft that has been positioned within a body vessel such that it is blocking an ostium of a branching vessel. The method allows for the apparatus 100 to be guided away from the metal strut to allow it to create a channel through the graft.

Many other methods and particular applications may be used with an apparatus of the present invention, and some embodiments of the method of the present invention may be used with an apparatus other than that specifically described in the "APPARATUS" section of this application.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the present invention has been described hereinabove by way of preferred embodiments thereof, it can be modified, without departing from the scope and nature of the subject invention as defined in the appended claims.

What is claimed is:

1. A method for creating a channel through a foreign material located in a septum of a heart at a site of a septal defect, said foreign material defining a material first surface and a substantially opposed material second surface, said channel extending through said foreign material at least partially between said material first and second surfaces, said method using an apparatus including an electrode, said method comprising:
   positioning said electrode substantially adjacent to said material first surface;
   energizing said electrode with a radiofrequency current; and
   using said electrode energized with said radiofrequency current to deliver energy into said foreign material to create said channel.

2. The method of claim 1, wherein said septum is selected from the group consisting of an atrial septum and a ventricular septum.

3. The method of claim 1, wherein said foreign material is included within an occluder extending across the septum at said septal defect.

4. The method of claim 3, wherein said occluder comprises one or more discs that are coupled by a bridging component.

5. The method of claim 4, wherein said channel comprises one or more channel portions.

6. The method of claim 5, wherein said apparatus is used to create at least one of the one or more channel portions within one of said one or more discs.

7. The method of claim 6, wherein said apparatus is used to create at least one of the one or more channel portions within each of said one or more discs.

8. The method of claim 7, wherein said one or more channel portions are substantially aligned.

9. The method of claim 8, wherein at least one of said one or more channel portions extends through said bridging component.

10. The method of claim 4, wherein the foreign material forms one or more graft portions of each of the one or more discs, and wherein each of the one or more discs comprises a supporting structure that is associated with the one or more graft portions for supporting the one or more graft portions.

11. The method of claim 10, wherein said one or more graft portions comprise one or more layers.

12. The method of claim 11, wherein said one or more layers are spaced apart from one another.

13. The method of claim 11, wherein said one or more layers comprise a synthetic material.

14. The method of claim 13 wherein said synthetic material is selected from the group consisting of a polyester, an expanded polytetrafluoroethylene (ePTFE), and a polyethylene terephthalate (PET) and fabrics thereof.

15. The method of claim 14, wherein said synthetic material comprises a woven polyester.

16. The method of claim 15, wherein said woven polyester is selected from the group consisting of a monofilament twill woven fabric and a multi-filament tubular woven fabric.

17. The method of claim 14, wherein said one or more layers comprise expanded polytetrafluoroethylene (ePTFE).

18. The method of claim 10, wherein said supporting structure comprises a metal scaffold.

19. The method of claim 18, wherein said method further comprises the steps of:
   detecting if said electrode is positioned substantially adjacent said metal scaffold; and
   upon detecting that said electrode is positioned adjacent said metal scaffold, guiding the apparatus away from the metal scaffold.

20. The method of claim 19, wherein the method further comprises the steps of:
   stopping the delivery of energy prior to guiding the apparatus away from the metal scaffold;
   repositioning the electrode substantially adjacent said foreign material; and
   re-energizing said electrode once it is positioned substantially adjacent said foreign material.

21. The method of claim 19, wherein the step of detecting uses a technique selected from the group consisting of: measuring output impedance, measuring output current, obtaining tactile feedback and using imaging techniques.

22. The method of claim 19, wherein the step of detecting is performed substantially automatically.

23. The method of claim 19, wherein said occluder comprises a single wire frame metal scaffold around a periphery thereof and wherein the step of guiding the apparatus away from the metal scaffold involves guiding the apparatus away from the periphery of the occluder.

24. The method of claim 1, wherein the step of delivering energy comprises generating a vapor layer around the electrode to facilitate arcing to create said channel within said foreign material.

25. The method of claim 1, wherein the step of delivering energy involves delivery of thermal energy to substantially melt said foreign material to create said channel therein.

26. The method of claim 25, wherein said foreign material comprises a synthetic material and wherein the foreign material is embedded within tissue.

27. The method of claim 26, wherein the step of delivering thermal energy comprises transferring thermal energy into said foreign material via the tissue upon energizing said electrode with said radiofrequency current.

28. The method of claim 1, wherein the step of positioning said electrode substantially adjacent to said material first surface comprises positioning said electrode substantially in contact with said material first surface to allow said electrode to substantially melt said foreign material upon energizing said electrode with said radiofrequency current.

29. A method of gaining access into a left side of a heart, the heart having a septum defining a septal defect, an occluder extending across said septum to repair said septal defect, said occluder comprising foreign material, said method using an apparatus including an electrode, said method comprising:
   positioning said electrode substantially adjacent to said foreign material within said occluder; and
   delivering energy into said foreign material by energizing said electrode with radiofrequency current to create a channel within said foreign material to allow the apparatus to cross the septum through said channel to gain access to the left side of the heart.

30. The method of claim 29, wherein the step of positioning said electrode comprises gaining access into the heart by inserting the apparatus through an inferior vena cava.

31. The method of claim 29, wherein the step of positioning said electrode comprises gaining access into the heart by inserting the apparatus through a superior vena cava.

* * * * *